(12) United States Patent
Akkurt et al.

(10) Patent No.: US 7,372,264 B2
(45) Date of Patent: May 13, 2008

(54) CONTAMINATION ESTIMATION USING FLUID ANALYSIS MODELS

(75) Inventors: Ridvan Akkurt, Kingwood, TX (US); Mark A. Proett, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 11/403,171

(22) Filed: Apr. 11, 2006

(65) Prior Publication Data

US 2006/0250130 A1 Nov. 9, 2006

Related U.S. Application Data

(63) Continuation of application No. 11/022,016, filed on Dec. 23, 2004, now abandoned.

(60) Provisional application No. 60/532,502, filed on Dec. 24, 2003.

(51) Int. Cl.
*G01V 3/00* (2006.01)
(52) U.S. Cl. ...................... 324/303; 324/300
(58) Field of Classification Search ............... 324/303, 324/300
See application file for complete search history.

(56) References Cited

U.S. PATENT DOCUMENTS

| 6,107,796 A | 8/2000 | Prammer |
| 6,274,865 B1 * | 8/2001 | Schroer et al. ........... 250/269.1 |
| 6,661,226 B1 * | 12/2003 | Hou et al. .................. 324/303 |
| 6,748,328 B2 | 6/2004 | Storm et al. |
| 6,825,657 B2 * | 11/2004 | Kleinberg et al. .......... 324/303 |
| 6,891,369 B2 | 5/2005 | Hurlimann et al. |
| 7,227,355 B2 * | 6/2007 | Chen et al. .................. 324/303 |

OTHER PUBLICATIONS

PCT International Search Report dated Nov. 2, 2005, International App. No. PCT/US04/43437.
PCT Written Opinion of the International Searching Authority dated Nov. 4, 2005, International App. No. PCT/US04/43437.

* cited by examiner

*Primary Examiner*—Louis M. Arana
(74) *Attorney, Agent, or Firm*—Jones, Day

(57) ABSTRACT

Methods and systems are described for estimating of the level of contamination of downhole fluid using physical property measurements, and mathematical modeling of contamination functions and fluid property mixing laws. The proposed approaches enable computation of estimates of the pumping time needed to achieve a certain contamination threshold level.

34 Claims, 19 Drawing Sheets

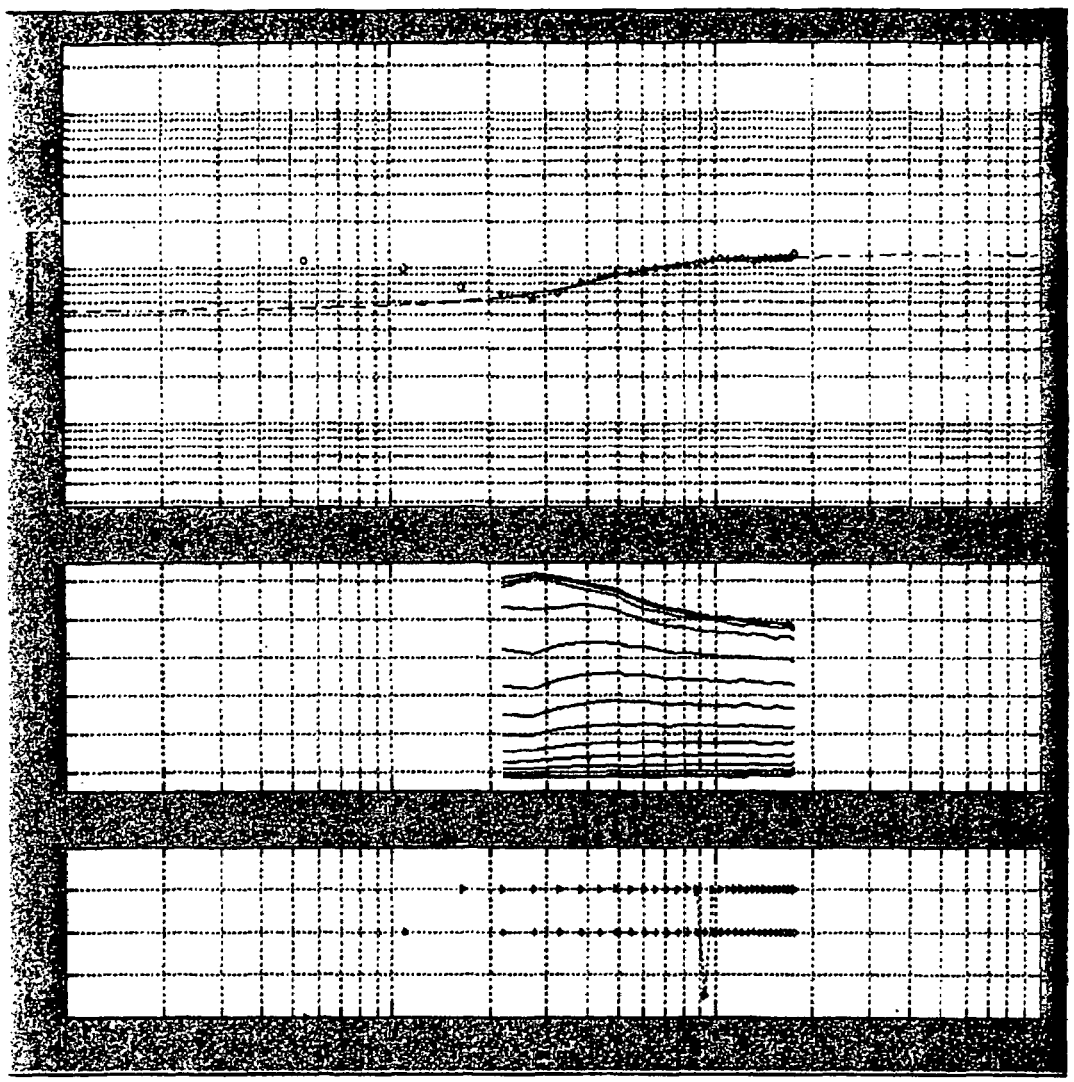

Figure 1. MRILAB data from a well drilled with OBM. The top plot shows viscosity index vs. time (min) in a log-log plot. Blue diamonds are data points included in the fit. The red circles are data points that were excluded from the inversion since the tool was not pumping. The reported laboratory contamination value is 4.0 %. The green curve is the fitted contamination function, based on the ArcTan Shifted 2 model (Equation 11). The estimated contamination, using the Modified Ahrrenius Mixing Rule (Equation 6) is 4.7%.

FIG. 4

CONTAMINATION ESTIMATION USING FLUID ANALYSIS MODELS

This application is a continuation of U.S. patent application Ser. No. 11/022,016 filed on Dec. 23, 2004, now abandoned which claims priority from provisional application Ser. No. 60/532,502, filed on Dec. 24, 2003, both of which are incorporated by reference for all purposes.

FIELD OF THE INVENTION

This invention relates to systems and methods for determining the level of mud filtrate contamination in formation fluids.

BACKGROUND OF THE INVENTION

Many oil industry applications require the analysis of downhole fluids. In the prior art this was typically done by bringing samples to the surface using sealed containers, and sending the samples for laboratory measurements. A number of practical limitations are associated with this approach. The main concern usually is that the samples taken to the surface may not be representative of the downhole geologic formation. This is due to the fact that only limited sample material from a limited number of downhole locations can be extracted and taken to the surface, and thus laboratory testing provides only an incomplete picture of the downhole conditions. Furthermore, samples are often contaminated with mud filtrate, and therefore are not truly representative of the native formation fluids.

More recently, fluid analysis became possible using pumpout formation testers that provide downhole measurements of certain fluid properties and enable the collection of a large number of representative samples stored at downhole conditions. Three families of such tools have been introduced in the past—the modular dynamic formation tester (MDT) by Schlumberger, the Reservoir Characterization Instrument (RCI) by Baker Atlas, and most recently the Reservoir Description Tool (RDT) by Halliburton. These tools are generally designed to obtain representative formation fluid samples and provide key petrophysical information to determine the reservoir volume, producibility of a formation, type and composition of the movable fluids, and to predict reservoir behavior during production.

One of the remaining problems encountered in the operation of such tools is to avoid contamination of the fluid naturally present in the formation with other fluids, in particular the various types of drilling muds used in drilling operations. Drilling mud, also known as drilling fluid, is typically pumped down the center of the hollow drill stem to emerge again at the surface of the borehole. It lubricates the drill shaft, cools the borehole, carries away the drilling detritus, and serves as a wetting-phase, which facilitates the flow of hydrocarbons from the formation and into the borehole. Various types of drilling muds are generally classified based on the type of filtrate used therein. The mud filtrate chosen dictates the mud's function and performance, as well as formation invasion effects.

There are two major types of mud filtrates: water-based and oil-based. Water-based mud (WBM) filtrates include, but are not limited to, freshwater, seawater, saltwater (brine) and others, or a combination of any of these fluids. In the oil-based mud (OBM), the filtrate is an oil product, such as diesel or mineral oil. More generally, oil-based mud is characterized as any type of non-aqueous fluid. For the purposes of the present disclosure, oil-based mud also includes the recently developed variety of oil mud that is also referred to as synthetic-based muds. These synthetic-based muds include, without limitation, olefinic-, naphthenic-, and paraffinic-based compounds. Dependent on the type of mud used in the drilling process, different factors affect the ability of the tool the accurately estimate the contamination levels at a given point during pumpout.

For WBM drilling, mixing with the formation fluid is considered an immiscible process, and determination of the degree of contamination of the fluid using is relatively straightforward. More challenging is the problem of estimating the degree of contamination in OBM drilling when attempting to obtain high quality formation fluid samples, because these mud filtrate fluids are mixed in the formation oil. This mixing can be immiscible or miscible, but either way complicate the determination of the degree of contamination (with immiscible invasion the fluids to not dissolve with each other but mix, with miscible mixing the fluids dissolve in a diffusion process). For example, the presence of even small volumes of oil-base filtrate in the sample can significantly alter the properties of the formation oil. As a result, in-situ quantification of the oil-base material contamination in the formation oil is difficult, and poorly quantified samples may not be representative of the formation fluid of interest.

Additional difficulties are presented in differentiating oil-based mud from connate oil when oil-based filtrate invades the formation. One method for differentiating oil-based mud from connate oil is disclosed in U.S. Pat. No. 6,107,796, owned by the assignee of the present invention, which is incorporated herein by reference. However, no reliable method has been provided for determining the level of contamination of mud filtrate in formation fluids.

The most frequently used prior art approach to estimating contamination has been based on the optical properties of the fluids entering a tool. Schlumberger provides for in-situ contamination estimation using an Optical Fluid Analyzer (OFA). Baker-Atlas also offers a service similar to the OFA. The OFA exploits the differences in the absorption spectrum (i.e., color contrast) between the OBM contaminant and the formation fluid to deconvolute the spectrum from a fluid measurement (see, e.g., U.S. Pat. Nos. 6,178,815, 6,274,865, 6,343,507 and 6,350,986, which are incorporated herein by reference for background). The OFA measures the optical density (OD) of the flowing fluid and uses empirical relationships to transform the OD into data on contamination by determining the composition of the measured absorbed light spectrum from the sample. Based on this absorption spectrum one can estimate the types of materials present in the fluid and the proportion of each material in the fluid. While the industry has learned how to interpret OFA data over the years, it still is not robust in certain applications where the color contrast is small, or is masked, as is frequently the case in light oils and condensates. One problem with this approach is that it assumes that the measured property is directly linked to the contamination, which may not necessarily be the case.

Another approach to contamination estimation is to use electrical resistivity methods, which involve the measurement of the apparent resistivity of fluids entering the tool. While these measurements are straightforward to implement and, for example, can easily distinguish between oil and water it cannot reliably distinguish contaminants in OBM situations. Various other sensors measuring optical properties, resistivity, capacitance and others within formation sampling tools have been used to estimate levels of fluid contamination during the pump-out phase, but no robust solution has been found yet.

A more recent approach to contamination estimation is provided by the use of nuclear magnetic resonance (NMR) measurements. NMR measurements of geologic formations may be done using, for example, the MRIL® tool made by NUMAR, a Halliburton company, and the CMR family of tools made by Schlumberger. Details of the structure of the MRIL® tool and the measurement techniques it uses are discussed in U.S. Pat. Nos. 4,710,713; 4,717,876; 4,717,877; 4,717,878; 4,939,648; 5,055,787; 5,055,78; 5,212,447; 5,280,243; 5,309,098; 5,412,320; 5,517,115; 5,557,200; 5,696,448; 5,936,405; 6,005,389; 6,023,164; 6,051,973; 6,107,796; 6,111,408; 6,242,913; 6,255,819; 6,268,726; 6,362,619; 6,512,371; 6,525,534; 6,531,868; 6,541,969; 6,577,125 and 6,583,621, all of which are commonly owned by the assignee of the present application. The CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466-485, 1992. NMR devices, methods and pulse sequences for use in logging tools are also in U.S. Pat. Nos. 4,350,955 and 5,557,201. The content of the above patents and publications is hereby expressly incorporated by reference for background. A brief discussion of the main NMR measurement parameters follows.

Basic NMR Properties and Measurement Parameters

NMR measurements are based on exposing an assembly of magnetic moments, such as those of hydrogen nuclei, to a static magnetic field. The assembly tends to align along the direction of the magnetic field, resulting in a bulk magnetization. A magnetic field having direction perpendicular to the static magnetic field is applied to rotate the magnetic moments away from the direction of the bulk magnetization. The rate at which the rotated moments return to the equilibrium bulk magnetization after application of the oscillating magnetic field is characterized by the parameter $T_1$, known as the spin-lattice relaxation time. $T_1$ values are in the range of milliseconds to several seconds.

Another related and frequently used NMR parameter is the spin-spin relaxation time constant $T_2$ (also known as transverse relaxation time), which is an expression of the relaxation due to inhomogeneities in the local magnetic field over the sensing volume of the fluid in the analyzer, e.g., a logging tool. In bulk fluids $T_2$ basically equals $T_1$, but may differ in heavy oil components, such as asphaltenes, resins, etc. Both relaxation times provide information about the properties of the formation fluid, such as the formation porosity and the composition and quantity of the formation fluid.

Another measurement parameter used in NMR is the formation diffusivity. Generally, diffusion refers to the motion of atoms in a gaseous or liquid state due to their thermal energy. The self-diffusion coefficient (D) of a fluid is inversely proportional to the viscosity ($\eta$) of the fluid, a parameter of considerable importance in borehole surveys. Stokes' equation yields that:

$$D \propto kT/\eta, \ (k=1.38 \times 10^{-23} \ J/K) \tag{1}$$

Viscosity and diffusivity are both related to the translational motion of molecules and therefore are interrelated. At higher temperatures T, a molecule contains more energy and can move faster against a given "friction" $\eta$, therefore D is proportional to the temperature. Diffusivity is a property that can be precisely determined by NMR techniques without disturbing or altering the fluid. The relationship $D \propto T/\eta$ has been verified over a wide range of viscosities at different temperatures and pressures by NMR spin-echo experiments.

Relationships involving the NMR relaxation times $T_1$ and $T_2$ must be examined with care. The applicability of expressions of the form:

$$T_1, \ T_2 \propto kT/\eta \tag{2}$$

is more limited than that of Eq. (1). The main reason is that gas/liquid mixtures have more than one relaxation mechanism: dipole-dipole for the liquid phase and mainly spin-rotation for the gas phase.

In a uniform magnetic field, diffusion has little effect on the decay rate of the measured NMR echoes. In a gradient magnetic field, however, diffusion causes atoms to move from their original positions to new ones, which also causes these atoms to acquire different phase shifts compared to atoms that did not move. This contributes to a faster rate of relaxation.

Recently, Halliburton introduced MRILab®, a logging tool with the ability to analyze key reservoir fluid properties, including fluid type, viscosity and gas-to-oil ratio (GOR), in real-time at reservoir temperature and pressure. MRILab® is based on NMR measurements and operates as a component of Halliburton's Reservoir Description Tool™ (RDT), making laboratory-quality measurements on reservoir fluids that are necessary for reservoir engineering and completion design. FIG. 5 shows a simplified diagram of a downhole NMR fluid analysis apparatus, such as the MRILab®, that provides NMR measurements to which the contamination estimation methods of the present disclosure can be applied in an illustrative embodiment. Fluids enter the device at the top and pass through two sections, referred to as polarization and resonance sections, respectively. Measurements are performed as the fluid flow passes through the device. U.S. application Ser. No. 10/109,072, which is hereby incorporated by reference, discloses details of this device, which are summarized for reference in Appendix A.

Turning back to the problem of contamination estimation, the fundamental difficulty in NMR-based approaches to such estimation is the lack of models that can predict the relaxation spectrum (i.e., the $T_1$ or $T_2$ spectrum) of a mixture of two fluids that are miscible. Existing NMR methods for estimating contamination, including when the MRILab® was first introduced, were based initially on a parameter called "sharpness." The sharpness of an NMR distribution is defined as:

$$S = \frac{N \sum_i a_i^2 \left( \sum_{i=1}^{N} a_i \right)^2}{(N-1)\left(\sum_i a_i\right)^2}, \ \text{for} \ 1 \le i \le N, \tag{3}$$

where $a_i$ are the amplitudes, and N is the number of components in a $T_1$ distribution. (See Bouton, J. et al. "Assessment of Sample Contamination by Downhole NMR Fluid Analysis", SPE-71714, presented at SPE ATCE, New Orleans, La. (2001) incorporated herein for background). Although it was thought that sharpness was sensitive to contamination levels down to 10%, experience has shown that sharpness in general is not a very robust indicator of contamination.

The driving idea behind the use of the sharpness parameter was that, while OBM has a narrow distribution (implying a lower S value), distributions associated with native crudes are broader. However, relaxation spectra of low viscosity crudes are also very narrow and in the low viscosity/high GOR case, it may not be possible to distinguish one species from the other. Furthermore, both bulk water and natural gas have narrow distributions. The information from sharpness is relative, in that it is an indicator of the changes taking place, but it may not be sufficient to define end point states quantitatively. Additionally, the sharpness parameter is derived from the $T_1$ distribution, which to a certain extent can be affected by the level signal-to-noise ratio (SNR) or distribution shape, which may lead to changes in the $T_1$ spectra that are unrelated to changes in contamination.

Given the difficulties using the prior art approaches, there exists a need for more accurate and robust methods for determining the level of contamination of mud filtrate in formation fluids.

SUMMARY OF THE INVENTION

The present invention provides a novel approach for determining the level of contamination in formation fluids. As used herein, a contaminant could be any fluid originating from mud filtrate that invades the reservoir during the drilling of a well; contamination (c) is the volume fraction of the contaminant in a fluid sample, where $0 \leq c \leq 1$. The following additional terms and expressions are used in the description of the proposed approach: a contamination function is a temporal function that substantially matches the behavior of the contamination fluid fraction while pumping a sample from an invaded zone. More generally, a contamination function is applicable to multiple-component fluid systems including systems comprised of miscible or immiscible liquids, including liquids containing dissolved, suspended or dispersed solids. Unless the context indicates otherwise, the term "fluid mixture" includes in its meaning a mixture of liquids (either miscible or immiscible) or a liquid containing soluble, suspended or dispersed solids. In accordance with the proposed approach, a contamination function is a mathematical model that may be derived, for example, through simulations or observation.

A mixing law (or mixing rule), as used in this disclosure, is a mathematical function that describes a property of a mixture in terms of the properties of its constituents. A mixing law would thus allow for the property of the mixture to be predicted if the weight or volume functions for the constituents, and the properties of these constituents, are known. Several examples of mixing laws are provided in the illustrative embodiment in which the physical property of the fluid being monitored is its viscosity. Different mixing laws may apply for other physical properties. In general, all that is required for the mixing law is to provide a mathematical expression that relates a property of a fluid mixture in terms of the constituent components properties (i.e., the values of such property for 0% and 100% contamination, respectively).

Using these definitions, the proposed contamination estimation approach is based on the use of a contamination function that describes the time behavior of a particular physical property of the mixture of fluids entering a tool, and a mixing-law or rule that is used to estimate the volume fractions of the constituent fluids given information about or measurements of the bulk physical property. In a specific illustrative embodiment, the physical property is viscosity, which is monitored indirectly using relaxation measurements (i.e., $T_1$ or $T_2$) obtained from an NMR fluid analyzer, such as the MRILab® fluid analyzer. Other physical properties that can be used in alternate embodiments include resistivity, capacitance, density, hydrogen index, compressibility, speed of sound, pumping pressures, optical density, and others.

In particular, the determined values of one or more of the above fluid properties over time are fit to a parameterized contamination function. By matching a contamination function to the fluid property measured over a period of time, the variables of this time function are determined, for example, through regression. Once the variables of the contamination function are determined, this function can predict how the fluid property changes over time. Then, the mixing law function that relates fluid fractions to the bulk fluid property can be used to estimate the actual contamination over past or future time periods.

In one type of embodiments, the contamination function used to predict the fluid property is either independent or substantially independent from the fluid fractions in the mixing law. These embodiments are referred to as uncoupled or loosely coupled contamination models. In other embodiments, the mixing laws are taken into account in tracking the bulk fluid property over time, resulting in a coupled contamination modeling. Different examples of such models are illustrated in the specific embodiments described below.

In specific embodiments monitoring viscosity using NMR measurements, several empirical contamination functions can be used in accordance with the proposed approach, including the exponential, the error and several versions of the arctan contamination functions, as defined below. In another aspect of this disclosure, the log-mean value of a NMR spectrum, in particular the log-mean $T_1$ value ($T_{1Lm}$) is shown to track the viscosity or other properties of the fluid and is used as an indirect property measurement. From the contamination function that best fits the empirical data, and a mixing law that includes estimates of the property values at two different contamination levels (typically at 0% and 100% contamination) one can compute the contamination index of the fluid (considered below) as a function of time. In the illustrative embodiments using viscosity as the monitored physical parameter, various mixing laws, such as those proposed by Todd et al., the power-law, various modifications of the Arrhenius law could be used, either coupled with or uncoupled from the select contamination function to estimate the desired contamination index.

It will be appreciated that the mathematical modeling approach based on the use of contamination function and mixing law can be used to estimate the level of contamination of a sample taken at a particular time, to compute the time required to reach certain contamination level during pumping, or to derive other parameters of interest during oil exploration.

Various modifications of this general approach can be used in practice. For example, the contamination function used in a particular experiment may be determined in advance through prior knowledge. Further, the accuracy of prediction can be improved if one has a priori knowledge about the monitored property value at 0% and 100% contamination. In alternative embodiments, several contamination functions corresponding to different physical properties can be used to monitor the time behavior of the fluid mixture entering the tool. These embodiments are based on the observation that in certain fluid mixtures one property may be more sensitive than others to the contaminant. Accordingly, an array of devices can be used in such embodiments to measure different fluid properties. Using this approach, for example, different contamination estimates can be combined into a single average contamination estimate. Individual contamination estimates may be weighted, possibly using nonlinear regression techniques. As is the case with MRILab® estimates of viscosity, the formation fluid properties can be more accurately predicted because the end points are used to determine the in-situ sample properties.

Accordingly, it is an object of this disclosure to provide methods for estimation of the level of contamination in the fluids flowing through an analyzer tool. Another object of the disclosure is to provide methods for estimating the pumping time needed to achieve a certain contamination threshold level. Yet another object of the disclosure is to provide methods for monitoring at least one physical property of the fluid entering the tool, such as its viscosity, and based on mixing laws that are known or can be derived use the monitored property to derive an estimate of the contamination level. Additional objective is to provide a computationally efficient algorithm for contamination estimation that can be implemented substantially in real time.

Accordingly, in one aspect, the invention is a method for estimating levels of contamination of formation fluids in a borehole, and a corresponding system implementing the steps of: (a) providing a first mathematical contamination function model which expresses a time behavior of one or more fluid properties of a mixture of formation fluids and contamination fluids drawn from a borehole, where said one or more fluid properties are sensitive to the fraction of contamination fluids in the mixture; (b) providing a second mathematical mixing law function model expressing at least one of said one or more fluid properties of a fluid mixture in terms of corresponding properties of formation fluids and contamination fluids in the mixture; (b) drawing fluids from the borehole into a fluid analyzer; (c) measuring at least one of said one or more properties of the drawn fluids by the analyzer; and (d) estimating the level of contamination in the fluids drawn from the borehole at one or more points in time based on the at least one measured fluid property and the provided mathematical models in step (a) and step (b).

In another aspect, the invention is a method for downhole formation testing, comprising the steps of: (a) providing measurement signals corresponding to a mixture of formation fluids and contamination fluids drawn from a borehole, the mixture entering a downhole fluid analyzer; (b) based on the provided measurement signals, determining parameters of a contamination function, which expresses the time behavior of one or more fluid properties of the fluid mixture drawn from the borehole; (c) computing from the determined contamination function of a value estimate of said one or more fluid properties for at least one low level of contamination and for at least one high level of contamination; and (d) computing a contamination index for the mixture of fluids drawn from the borehole at different time instants based on the computed value estimates and a fluid mixing law relating properties of the drawn fluids in terms of the corresponding properties of the formation fluids and the contamination fluids.

Other aspects of the disclosure are discussed in the following detailed description, and are defined in the attached claims.

BRIEF DESCRIPTION OF THE DRAWINGS

FIG. 4 illustrates the use of NMR fluid analyzer measurements for contamination estimation in one embodiment;

DETAILED DESCRIPTION OF THE PREFERRED EMBODIMENTS

Figure 1A:
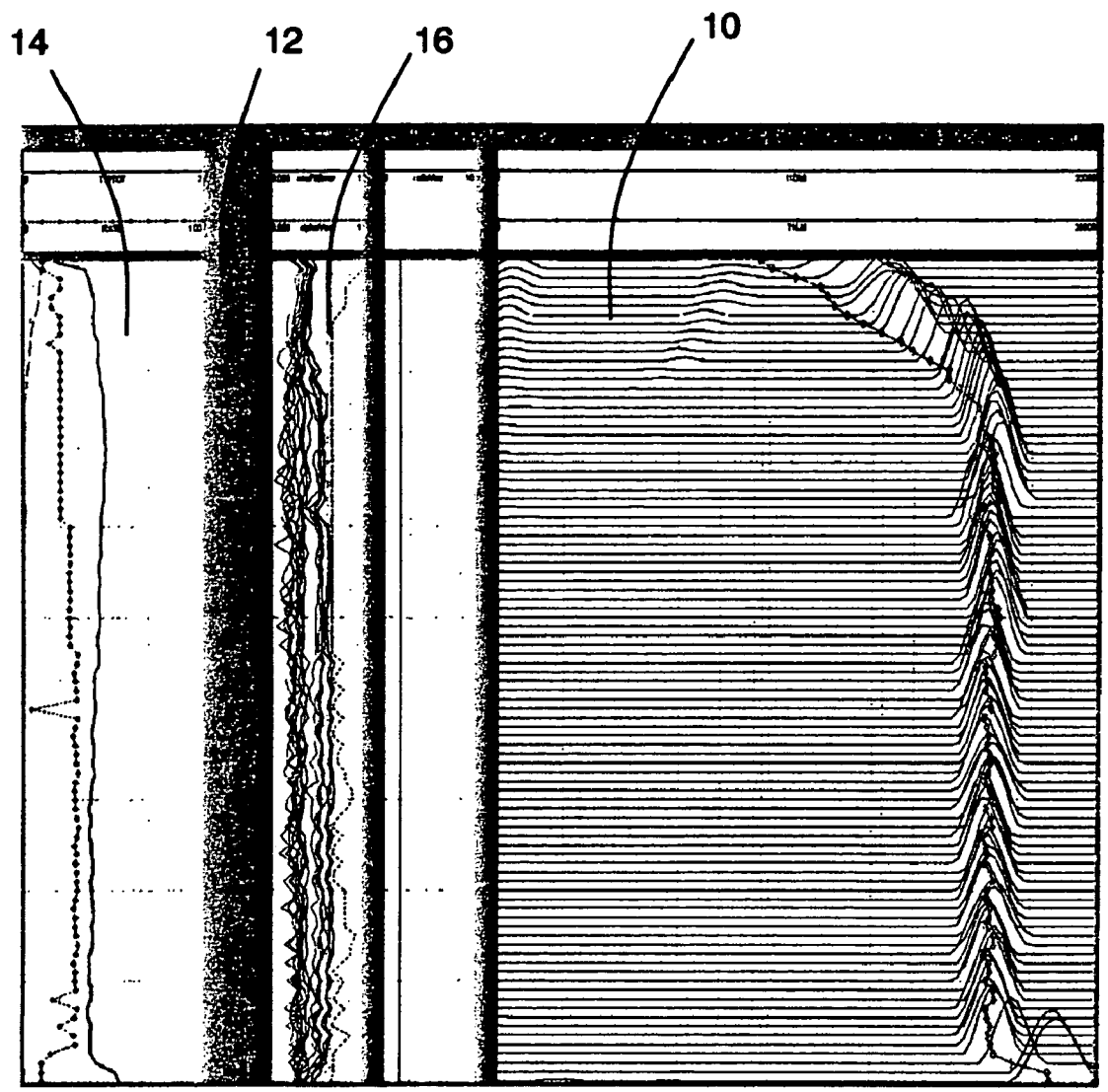
FIGS. 1A and 1B show $T_1$ data and data analysis from several experiments performed under downhole conditions.
Figure 1B:
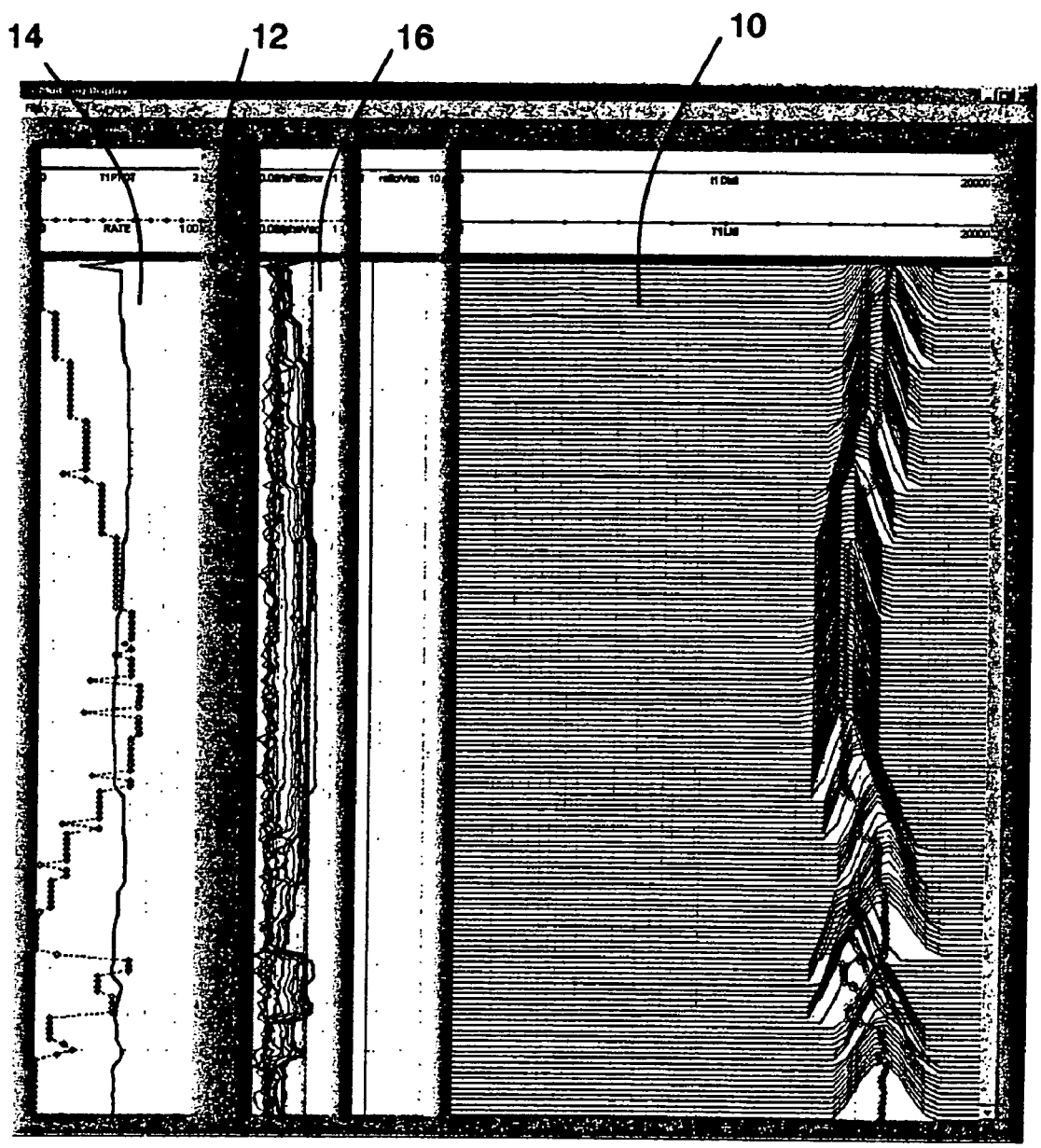

The principal objective of contamination estimation is to secure fluid samples with low levels of contamination for proper Pressure Volume Temperature (PVT) analysis. Another objective is to predict when to stop pumping with a high level of confidence as to not waste rig time on unnecessary clean up pumping. Improved contamination estimates increase the accuracy of the log analysts' data interpretation, and help to provide better estimates of permeability and anisotropy from the pumpout data.

The proposed contamination estimation approach described in different embodiments below is based on the use of one or more contamination functions describing the time behavior of a particular physical property of a mixture of fluids entering a tool; and one or more mixing-law models that can be used to estimate the volume fractions of the constituent fluids given information about or measurements of the physical property. In a specific illustrative embodiment considered below, the physical property is viscosity, which is monitored using indirect measurements, i.e., $T_1$ measurements obtained from an NMR fluid analyzer. Other physical properties that can be used in different embodiments include resistivity, capacitance, density, hydrogen index, compressibility, speed of sound, pumping pressures, optical density, and others. Contamination estimation in accordance with this approach is done for both miscible fluids (i.e., OBM applications) and immiscible fluids (i.e., WBM applications). Accordingly, different contamination models are based on different set(s) of specific assumptions or requirements, and each model may have its particular strengths over the others. Mathematically, the time changes of the contamination index CI over the pumping can be expressed as:

$$CI(t)=fc(\alpha_1, \alpha_2, \alpha_m, t) \quad (4)$$

where $\alpha_{1/2}$ are the end points in the property values (0% and 100% contamination), and $\alpha_m$ is the measured property value. Turning first to the mixing law modeling problem, in the simplest case a bulk fluid property may be assumed to depend linearly on the corresponding properties of the constituent fluid volume fractions (i.e., on a linear combination of the contamination and virgin reservoir fluids). For example, light absorption is proportional to the volume fraction of the constituent fluids. Thus, if the end point properties of the fluid mixture (0% and 100% contamination) are known or can be estimated, and there is sufficient contrast in the property of the contaminant and the reservoir fluid, measurement of the bulk property enables straightforward contamination determination.

In the more general case, however, the mixing law is non-linear and the end point property values are unknown. Consider for example viscosity. As set forth in Eq. (2), viscosity is inversely proportional to the $T_1$ relaxation parameter in a NMR measurement, which can be obtained substantially in real time using a fluid analyzer. Accordingly, models based on the time or $T_1$ domain NMR signatures of the fluids can be used for contamination estimation in immiscible fluids, as discussed below. But such models in general are unsuitable for miscible fluids, because there is no simple mixing rule that relates the end-point NMR properties to the measured NMR property as a function of the constituent fluid component saturations.

In accordance with one important aspect of the disclosure, the approaches in this application are based on the observation that the log-mean value of an NMR parameter varies with contamination over time. Previous research has shown that the echo amplitudes in NMR measurements of a fluid entering a fluid analyzer change with time, and as a result have developed time dependent models where an empirical relationship was used to curve fit the echo amplitude changes and to relate the combined time decays to contamination. The embodiment(s) discussed below are based on the observation that log-mean $T_1$ ($T_{1Lm}$) shifts with contamination over time, rather than on the tracking of individual $T_1$ amplitudes. This observation is also applicable to the variation in the log-mean value of other NMR parameters with contamination over time.

In particular, the log-mean $T_1$ shift over time can be attributed to changes in viscosity as the fluid being pumped changes to different proportions of filtrate oil or water. A study of field results from an NMR fluid analyzer, as well as multi-phase forward modeling results, shows that contamination (c) varies with time (t) in a predictable pattern. Therefore, a possible solution to the contamination estimation problem for miscible fluids is to use an indirect property, such as $T_{1Lm}$, the log-mean $T_1$. $T_{1Lm}$ is inversely related to viscosity and can be used to estimate contamination when combined with a mixing law that is based on viscosities of two miscible fluids. Because the log-mean $T_1$ is used in the illustrative embodiments discussed below, some explanation and definitions are in order.

Calculation of Log-mean $T_1$ Values

In one embodiment, the contamination estimation models are applied to a log-mean value derived from one or more NMR measurements. The derivation of the log-mean value of a $T_1$ spectrum is presented below in a preferred embodiment. However, similar relations apply for deriving the log-mean value of other spectra obtained by NMR measurements, such as a $T_2$ spectrum or diffusivity spectra. Modifications and variations of the approaches disclosed herein, based on the use of a log-mean value of an NMR-based measurement will be apparent to one of ordinary skill in the art without undue experimentation.

As noted, in a preferred embodiment, the contamination estimation models are applied to log-mean $T_1$ values. The log-mean $T_1$ of a $T_1$ spectrum is calculated using the expression:

$$\log(T_{1Lm}) = \frac{\sum_j a_j \log(T_{1j})}{\sum_j a_j}, \quad (5)$$

where $\alpha_j$ are the amplitudes of a given $T_1$ spectrum, and j is the number of $T_1$ bins used in the inversion.

The typical range for the $T_1$ relaxation parameter is from about 1 ms to 20,000 ms. In one embodiment, all of the amplitudes that cover the measured range are used in the computation of $T_{1Lm}$. In alternative preferred embodiments, $T_{1Lm}$ may be computed for a subset of $T_1$ spectrum values, either to reject noisy components in the spectrum, or to focus around a certain $T_1$ range, where the change in energy contained in that particular band has a large dynamic range as a function of time. In alternate embodiments, the $T_1$ spectrum can be subdivided into several bands, and the corresponding $T_{1Lm}$ for each band is then computed. This subdivision can be based on computational simplicity or observations concerning the temporal characteristics of different $T_1$ sub-bands.

Accordingly, in one embodiment, contamination estimation is based on the use of one or more of the bands of a subdivided $T_1$ spectrum. A band of the $T_1$ spectrum can be selected on the basis of one or more desired criteria, such as maximum dynamic range, longest center $T_1$ value, and others.

In another embodiment, contamination estimation is based on a combination of the bands of the subdivided $T_1$ spectrum. The contamination estimates resulting from the application of the one or more contamination estimation models to different bands of the subdivided $T_1$ spectrum can be combined in a number of different ways, either linearly or non-linearly, to form an averaged contamination estimate.

FIGS. 1A, B give an example of the computation of $T_{1Lm}$ from the $T_1$ distributions in OBM logging experiments. Panel 10 shows MRILab® $T_1$ measurements (in milliseconds) from ninety-one successive OBM logging experiments (uncorrected for flow). Vertical scale 12 shows the experiment number in sequential order, from earlier times (top) to later times (bottom). Panel 14 shows the apparent hydrogen index for each experiment, which is derived from the area under the $T_1$ distribution (discussed below). The hydrogen index is about 0.7 for a majority of the experiments. The tool has stopped pumping at the very bottom of the chart, therefore at the very end the hydrogen index is about 1. The fit error for each wait time group is shown in panel 16. Panel 10 also shows the corresponding $T_{1Lm}$ (connected diamond markers), calculated from the MRILab® $T_1$ distributions for each experiment (solid curves). Variations in the $T_1$ distributions and $T_{1Lm}$ include contributions due to changes in contamination and flow rate. The center of the $T_1$ distributions is around 3.5 seconds for a majority of the experiments.

Viscosity Estimates Using NMR Measurements

The viscosity of a crude oil can be estimated from the $T_{1Lm}$ value by the following empirical relationship:

$$\eta = 0.009558 \frac{T_k}{T_{1Lm}}, \quad (6)$$

where $T_{1Lm}$ is the log-mean $T_1$ value, $T_k$ is the absolute temperature in degrees Kelvin, and viscosity is in units of centipoise. A poise is a centimeter-gram-second unit of dynamic viscosity, equal to one dyne-second per square centimeter. The relationship between the viscosity of crude oil and the log-mean value of other NMR parameters can be empirically estimated or approximated using Eq. (6) in combination with a measurement of the log-mean $T_1$ value, and applied to any of the viscosity mixing rules and/or contamination models presented below or otherwise known in the art. The $T_{1Lm}$ can be used to estimate contamination when combined with a mixing law that is based on viscosities of two miscible fluids, as discussed in further detail below.

The viscosity relationship of Eq. (6) is an approximation for use mainly with "dead" oils. For "live" oils, which contain gas components, a better viscosity estimate is:

$$\eta = 0.009558 \frac{T_k}{f(GOR)T_1} \quad (7)$$

where $T_{1Lm}$ is approximated by $T_1$ times a function of the gas-oil-ratio (GOR).

Viscosity Mixing Rules

As noted, a mixing law or rule is a mathematical expression that describes a property of a mixture in terms of the properties of its constituents. This allows for the property of the mixture to be predicted if the weight or volume fractions or functions for the constituents, and the properties of the constituents are known.

It has been concluded that no single mathematical expression could represent the viscosities of all hydrocarbon mixtures. See Shu, W. R., "A Viscosity Correlation for Mixtures of Heavy Oil, Bitumen, and Petroleum Fractions", SPEJ, June, 277-282 (1984). This accounts for the variety of mixing rules that are known or can be developed, all of which may be used in accordance with different embodiments.

Several empirical viscosity mixing rules exist that relate the measured viscosity of a miscible mixture to the volume fractions of the end-point viscosities, i.e., to the viscosity of each individual component. The four most commonly used relations are listed in the following table:

$$\eta_m = \frac{\eta_1 \eta_2}{[s_1 \eta_2^{1/n} + s_2 \eta_1^{1/n}]^n}, \quad \text{(Todd et al).} \quad (8)$$

$$\eta_m = [s_1 \eta_1^n + s_2 \eta_2^n]^{1/n}, \quad \text{(Power-Law),} \quad (9)$$

$$\ln(\eta_m) = s_1 \ln(\eta_1) + \ln(\eta_2), \quad \text{(Arrhenius),} \quad (10)$$

$$\ln(\eta_m) = \frac{as_1}{as_1 + s_2} \ln(\eta_1) + \left[1 - \frac{as_1}{as_1 + s_2}\right] \ln(\eta_2), \quad \text{(Modified Arrhenius).} \quad (11)$$

In the above equations, $\eta_m$ is the measured viscosity of the mixture, $\eta_1$ and $\eta_2$ are the end point viscosities (i.e., the viscosity of each component of the mixture), $s_1$ and $s_2$ are their respective volume fractions (or saturations), while n and a are empirically determined non-negative constants. Note that $s_1 + s_2 = 1$, and if it is taken that $c = s_1$, then $s_2 = 1 - c$, where c is the level of contamination.

The value of n is typically 4 in the viscosity mixing rule in Eq. (8), developed by Todd, M. R., et al. "The Development, Testing and Application of a Numerical Simulator for Predicting Miscible Flood Performance," Journal of Petroleum Technology (1972).

In Eqs. (9) or (10), $s_1$ and $s_2$ may represent a mass fraction, a mole fraction, or a volumetric fraction. In exponent n in the Power-Law mixing rule in Eq. (9) is an adjustable value that depends upon the components and the proportions in the mixture. The Arrhenius rule in Eq. (10) is also known as the log mixing rule.

The fourth mixing rule in Eq. (11), is a modified version of the classic Arrhenius expression, which was originally proposed by Lederer, E. L., Proc. World Pet. Cong., vol. 2, pp. 526-28, London (1933). The constant a is found empirically and has values between 0 and 1. The volume fractions $s_1$ and $s_2$ are associated with the contaminant and the oil, respectively. Rhames et al. examined this equation for mixtures with low viscosity ratios $\eta_1/\eta_2$, and found that this function expression provided an excellent fit to their data. See Rhames, M. H., et al. "Viscosity Blending Relationships of Heavy Petroleum Oils", Analytical Chemistry, vol. 20, pp. 912-915 (1948). Other researchers used the same functional expression for mixtures of high viscosity ratios typical of bitumen and solvent fractions. Shu, W. R., "A Viscosity Correlation for Mixtures of Heavy Oil, Bitumen, and Petroleum Fractions", SPEJ, pp. 277-282 (1984). Shu correlated the parameter with properties characteristic of the individual mixture components including the viscosity and the densities of solvent and oil.

As described below, in different embodiments one or more of the viscosity mixing rules can be applied to the log-mean value of an NMR spectrum, or the log-mean value of one or more subdivided bands of the NMR spectrum, for estimating the viscosity of a formation fluid contaminant and/or a hydrocarbon phase in a formation fluid. The contamination estimation methods in accordance with the approach proposed herein will vary according to the chosen viscosity mixing rule. Several variations of the contamination estimation models are described below.

Modeling the Contamination Function

In addition to the mixing rules considered above in illustrative embodiments, the contamination estimation approach in this application is based on the use of a contamination function, which is a temporal function that substantially matches the behavior of the contamination fluid fraction while pumping a sample from an invaded zone.

As a result of a large number of simulations with miscible and immiscible mud systems, as well as studying the behavior of MRILab® field results, the following models have been developed to describe the time dependent behavior of the contamination function c(t), in accordance with different embodiments:

$$c(t) = a_3 + a_1 \arctan\left(\frac{t^p}{a_2}\right), \quad \text{(ArcTan),} \quad (12)$$

$$c(t) = a_3 - a_1 \exp(-t^p/a_2), \quad \text{(Exponential,)} \quad (13)$$

-continued $$c(t) = a_3 + a_1 \arctan\left(\frac{t-a_4}{a_2}\right), \quad \text{(ArcTan-Shifted 1)}, \quad (14)$$

$$c(t) = a_3 + a_1 \arctan(t^p + a_2), \quad \text{(ArcTan-Shifted 3)}, \quad (15)$$

$$c(t) = a_3 + a_1 \arctan\left(\frac{t^p}{a_4} + a_2\right), \quad \text{(ArcTan-Shifted 3)}, \quad (16)$$

$$c(t) = \frac{1}{2} - \frac{1}{2}\mathrm{erf}\left[a_2 \log\left(\frac{t}{a_1}\right)\right], \quad \text{(Error Function)}. \quad (17)$$

In the models above, $a_1$, $a_2$, $a_3$, $a_4$ and p are constants, and erf is the error function defined as:

$$\mathrm{erf}(x) = \frac{2}{\sqrt{\pi}} \int_0^x e^{-t^2} dt. \quad (18)$$

The idea in accordance with the proposed approach is to fit the determined values of one or more fluid properties, such as viscosity, over time to a parameterized contamination function as shown in the table. By matching a contamination function to the fluid property measured over a period of time, the variables of this time function are determined, for example, through regression. Matching could be done over the individual functions listed. For example, the error function in Eq. (17) is a solution for well-defined cases of invasion and these curves have a strong resemblance to the form of a sample quality function given by $f_{sq}(t)=1-c(t)$, where $f_{sq}$ is the sample quality (0 to 1, dimensionless), c(t) is given by Eq. (17), t is time, $a_1$ is time at 50% contamination, and $a_2$ is the time scaling parameter. A detailed numerical simulation study was performed to determine the pumpout contamination versus time.

Figure 2:
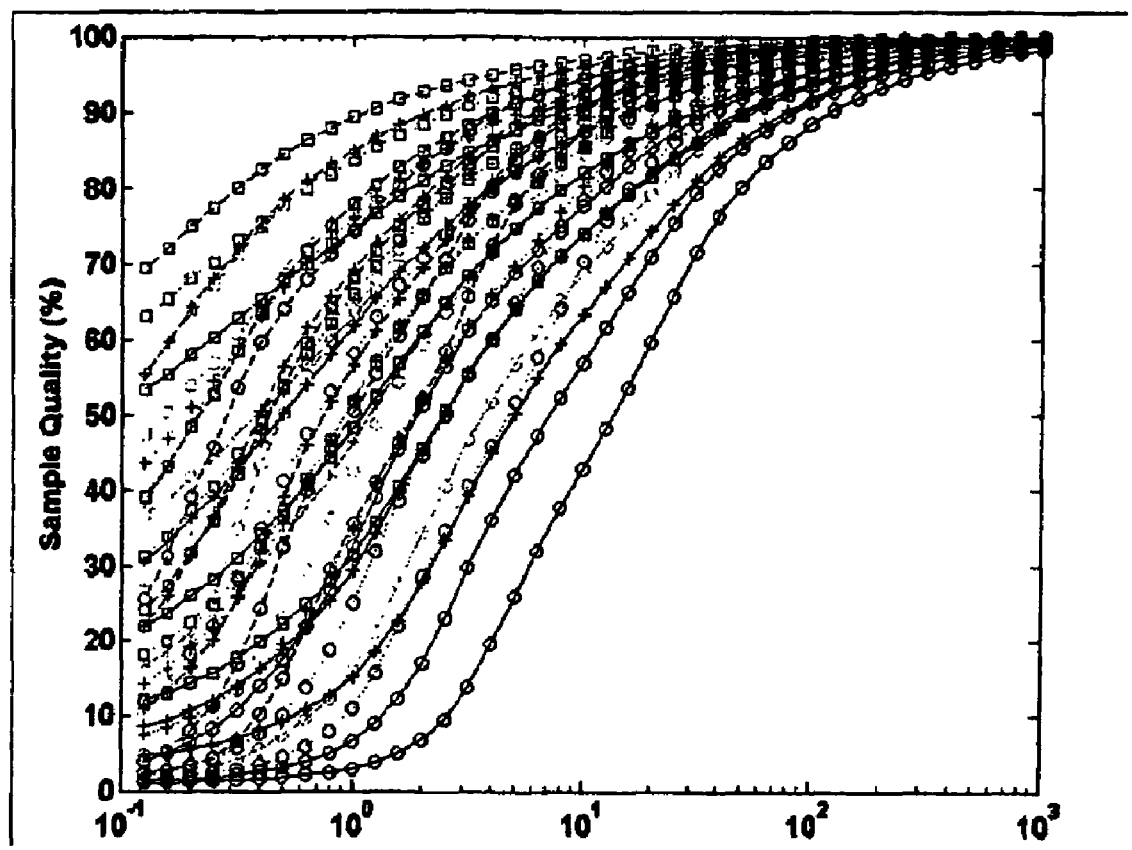
FIG. 2 shows the results of sample quality vs. time (seconds) simulations for an oil-based mud (OBM) systems, where sample quality is given in percentages.
Figure 3:
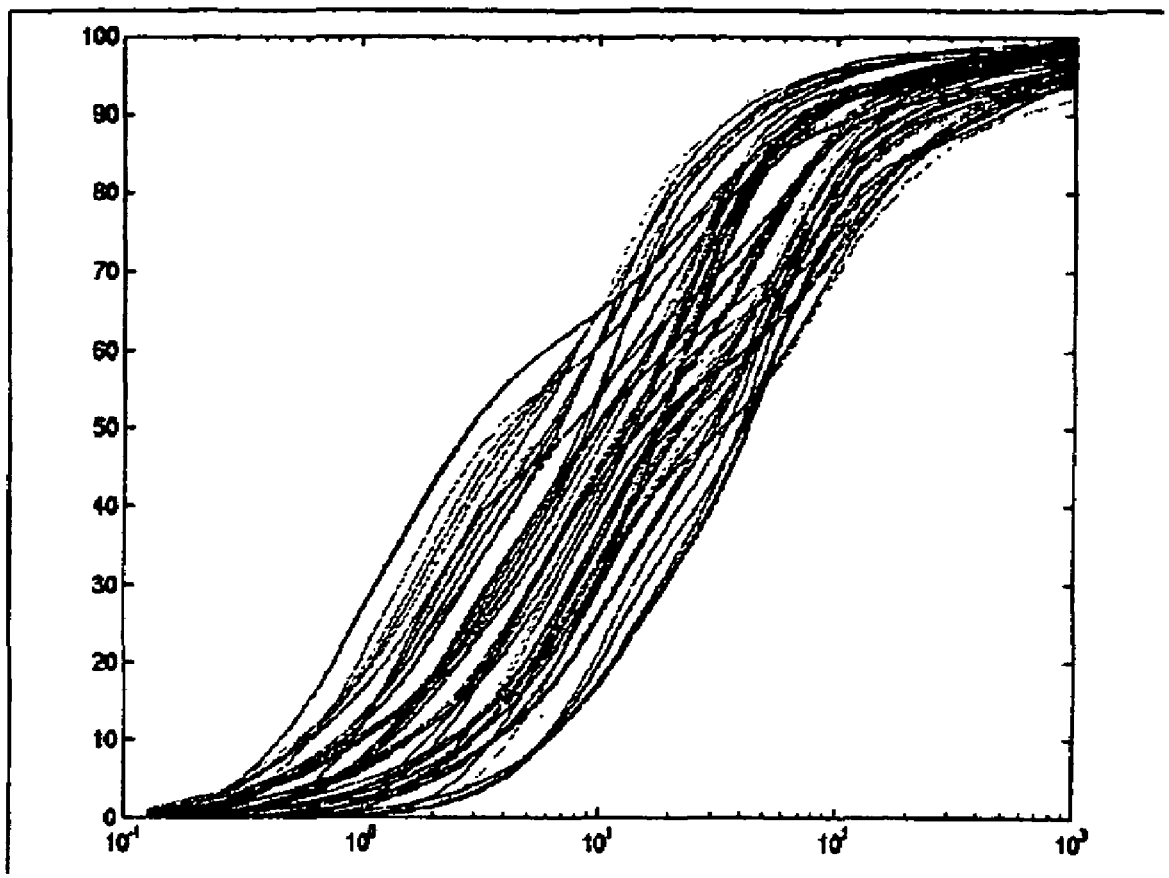
FIG. 3 shows the results of sample quality vs. time (seconds) simulations for a water-based mud (WBM) system at 10 cc/sec pumping rate, where sample quality is given in percentages.

FIG. 2 shows the results of a large number of sample quality simulations with OBM systems using a sample quality function developed from the Landmark VIP reservoir simulator. Invasion was simulated first and used as the initial condition for the sampling pumpout sequence. The contamination curves were developed by tracking the volume fraction of the fluids entering the sampling tool. FIG. 3 shows how these simulations can be closely mimicked using the Error Function contamination function in Eq. (17). The parameter $a_1$ controls the shape of the curve (inflection point at 50% contamination) and has units of time. The dimensionless parameter $a_2$ scales the independent variable t. Typical ranges for $a_1$ and $a_2$, for OBM systems are $0.50 \leq a_1 \leq 100$, and $0.50 \leq a_2 \leq 0.75$.

The other contamination functions in the preceding table (Eqs. 12-16) can be matched to the simulated curves in a similar manner. Experience with field data, the mixing models and the sensor data aids in determining the best contamination model for a particular fluid property. More specifically, in a preferred embodiment, matching can be done by defining a vector ρ of unknown parameters: $\rho = [a_1, a_2, a_3, a_4, p]^T$. The objective is to adjust the vector of unknown parameters such that the time function c(t) matches the measured fluid property data. Thus, to determine ρ, in a specific embodiment a nonlinear least squares problem is posed and solved such that the following function is minimized, as known in the art:

$$\min_\rho \sum_{i=1}^N (\hat{\eta}_m(i) - \eta_m(i))^2$$

where i denotes an experiment, N denotes the total number of experiments in the dataset and the measurement is done using estimated values for the bulk fluid viscosity. Based on two recent studies of laboratory data, as well as MRILab® data it appears that the Eq. (16) has the greatest potential of accurate results. After the optimizer has determined the unknown parameters, the viscosity index of the contaminant $\eta_1$ and of the formation fluid $\eta_2$ is determined by extrapolating c(t) to t=0; and t=∞ respectively.

It will be appreciated that the application of the contamination estimation methods of this disclosure vary according to the contamination model chosen to be applied, for example, i.e., to an NMR spectrum, or to one or more subdivisions of the NMR spectrum. The methods may also change dependent on whether the contamination model is applied in conjunction with one or more mixing rules.

Variations of the Miscible Fluid Models (MFMs)

The above modeling is applicable to OBM applications, in which it is assumed that contamination is the result of mixing miscible fluids. Accordingly, the proposed models are termed Miscible Fluid Models (MFM). As noted before, in the case of miscible fluids, the challenge in contamination estimation is to find a mixing rule that relates the end-point fluid properties to a measured bulk fluid property as a function of their saturations; and the basic approach to MFM in preferred embodiments is to relate the viscosity of the mixture to the log-mean value of an indirect property measurements, such as the log-mean $T_1$ ($T_{1Lm}$).

This section provides four variations of the contamination estimation methods used in different embodiments, based on four different contamination estimation models. It will be appreciated that other contamination estimation models can be formulated from variations of the approaches discussed herein. While the contamination estimation models are described relative to $T_1$ spectra and the log-mean $T_1$ value ($T_{1Lm}$), the variations of the contamination estimation methods, based on contamination estimation models that are expressed in terms of other NMR measurement parameters, including, but not limited to, $T_2$ and diffusivity measurements, are also envisioned and will be appreciated by those of skill in the art.

Implicit Log-mean $T_1$ (ILMT1)

At present, there is no model that can fully predict the $T_1$ spectrum of a miscible mixture, given the $T_1$ spectra of the end points and their volume fractions in the mixture. In the real-life cases, strictly speaking neither the end point spectra, nor the volume fractions are known. However, given that $T_{1Lm}$ is correlated to viscosity and that the viscosity mixing laws predict two very clearly defined end points, one can reason that $T_{1Lm}$ is a bounded function, where the asymptotes at time zero and infinity correspond to the $T_{1Lm}$ of the contaminant and the formation fluid (e.g., the crude), respectively.

A first embodiment of the invention, called the Implicit Log-mean $T_1$ (ILMT1) model, provides that the two limits can be defined as follows:

$$\lim_{t \to 0} c(t) = T_{1Lm,0} \tag{19}$$

$$\lim_{t \to \infty} c(t) = T_{1Lm,\infty} \tag{20}$$

In the ILMT1 model, the $T_{1Lm}$ values are fit using a contamination model in order to compute the two limits given in Eqs. (19) and (20). Given these two quantities, the contamination level at time $t_k$ is determined in the ILMT1 model using the relation:

$$c(t_k) = \frac{|T_{1Lm}(t_k) - T_{1Lm,\infty}|}{|T_{1Lm,0} - T_{1Lm,\infty}|} \tag{21}$$

The parameter $c(t)$ is assumed to conform to the shape of one of the contamination function models discussed above. The problem to be solved is an over-determined non-linear least squares problem, where the parameters in the contamination function are solved using well-known nonlinear least-squares (NLLS) solvers.

In one embodiment, the level of contamination of a formation fluid or an estimation of the pumping time needed for achieving a given contamination level can be provided based on application of the ILMT1 contamination estimation model. In a specific embodiment, using the ArcTan-Shifted 2 contamination model in Eq. (15), the model is solved (using NLLS techniques) to compute the parameters $a_1$, $a_2$, $a_3$, and p. The limits of the function are then calculated using the computed parameters to obtain the $T_{1Lm}$ for the end-points (see Eqs. 19 and 20). Finally, Eq. (21) is used to compute the contamination at time $t_k$. The contamination estimate at time $t_k$ can then be used to estimate the pumping time necessary for achieving a given contamination level. This estimation can be based on examining the time-function of the contamination parameter.

In a second aspect of the ILMT1 model, the inverse of the log-mean value (i.e., $1/T_{1Lm}$) can be substituted for the log-mean value ($T_{1Lm}$), and the exact same steps can be carried out. The main advantage of this approach is that the inverse of the log-mean value of the NMR parameter could provide information about other materials properties, e.g., $1/T_{1Lm}$ is directly proportional to viscosity.

Explicit Log-mean $T_1$ (ELMT1)

The Explicit Log-mean $T_1$ (ELMT1) model, used in another embodiment, where the relationship between the log-mean $T_1$ and viscosity is used explicitly, is an extension of the approach described above.

In the ELMT1 model, the $T_{1Lm}$ values are fit using a contamination model, as in the ILMT1 model, in order to compute the two limits given in Eqs. (19) and (20). The two end point viscosities are obtained from the end point $T_{1Lm}$ values using Eq. (6), where:

$$\eta_1 = 0.009558 \frac{T_k}{T_{1Lm,0}}, \tag{22}$$

$$\eta_2 = 0.009558 \frac{T_k}{T_{1Lm,\infty}}, \tag{23}$$

Finally, a viscosity mixing rule, e.g., Eqs. (8) through (11), is applied to compute $c(t_k)$ for a given mixture. For example, Eq. (8) can be recast in terms of c using the relation that $s_1 = c$, and $s_2 = 1 - c$:

$$\eta_m = \frac{\eta_1 \eta_2}{[c\eta_2^{1/n} + (1-c)\eta_1^{1/n}]^n}, \tag{24}$$

after which the equation is solved for $c(t_k)$. It will be appreciated that contamination estimates at different times can be used to compute the time necessary to achieve a given contamination level at a given pump time.

Coupled Log Mean $T_1$ (CLMT1)

In the ELMT1 model, the contamination model and the mixing rule are applied in two discrete steps. However, in a third embodiment of the invention, referred to as the Coupled Log-Mean $T_1$ (CLMT1) model, the contamination model is coupled with the viscosity mixing rule. The resulting nonlinear system is then solved for a greater number of unknowns.

In a first aspect according to the third embodiment, the ArcTan contamination model given in Eq. (12) is coupled with the Arrhenius viscosity mixing rule given in Eq. (10), which results in the following non-linear couple system:

$$\ln\left(0.009558 \frac{T_k}{T_{1Lm}}\right) = \left\{\left(a3 + a1 \arctan\left(\frac{t^p}{a_2}\right)\right) \ln(\eta_1)\right\} + \left\{\left(1 - a_3 - a_1 \arctan\left(\frac{t^p}{a_2}\right)\right) \ln(\eta_2)\right\} \tag{25}$$

In a second aspect according to the third embodiment, the viscosity mixing rule of Todd et al. given in Eq. (8) is coupled with the error function contamination model $c(t)$ given in Eq. (17), which results in the following non-linear couple system:

$$\eta_m = \frac{\eta_1 \eta_2}{[c(t)\eta_2^{1/n} + (1-c(t))\eta_1^{1/n}]^n}, \tag{26}$$

where the value of n is typically 4, $\eta_m$ is the measured viscosity, $c(t)$ is the contamination level at time t, $\eta_1$ is the viscosity of the OBM, and $\eta_2$ is the viscosity of the native crude.

There are many other possible specific forward models for the CLMT1 model resulting from the coupling of a contamination function model with a viscosity mixing rule, given the four viscosity mixing rules and the six contamination function models described above, and other contamination models or viscosity mixing rules available to one of ordinary skill in the art. It is intended that such alternative contamination function and mixing law models are within the scope of the present invention and the appended claims.

Immiscible Fluids Models (IFM)

An assumption implicit in the MFM models and methods is that the mixing is miscible. However, in many instances the distinction between miscible and immiscible may disappear, and models specifically designed for immiscible mixing (i.e., in WBM applications) may be necessary for a particular application.

Another embodiment in accordance with this disclosure provides the Immiscible Fluid Model (IFM), which is designed for WBM applications. The IFM can be applied for NMR measurements either in the time domain or in the $T_1$ domain. In preferred embodiments, the NMR data derives from MRILab® $T_1$ measurements. An assumption of the IFM model is that the measured response, whether in the time or in the $T_1$ domain, is a linear combination of the signatures of the two end members, where the weighting is governed by the contamination level. The IFM method used in a preferred embodiment includes two steps. First, the two end members are determined from the available data. Given the end-member signatures, the contamination levels are then determined in the second step.

The first step of the IFM model is to determine the end-point signatures x and y. The major unknowns in this step are the NMR signatures of the two fluids (either in time, or $T_1$ domain), in addition to the contamination levels. If the NMR signature of the two fluids at the two end-point, i.e., the NMR signal of the uncontaminated fluids, is represented by x and y, and given a data matrix of:

$$B=\{b_1, b_2, b_3, \ldots, b_k\} \quad (26)$$

where $b_k$ is the kth column representing the NMR measurement corresponding to the kth experiment, then the measurements are modeled as follows:

$$b_k = c_k x + (1-c_k) y \quad (27)$$

Equations (26) and (27) are given as discrete functions only for ease of notation, and the IFM is not so limited. The $c_k$ of Eq. (27) are not ordered in time, in that the unknown vectors x and y would be the same if the columns of B are reshuffled. As a result, an advantage of the IFM model is that the end point vectors can be estimated independent of the dynamics of fluid flow. The contamination function is generally a monotonically decreasing function of time. However, if the flow rate changes during the measurements, e.g., if pumping is stopped, the mud filtrate can flow back in around the probe in the analyzer. This may result in a higher level of contamination when the pump starts again. As a result, if contamination is modeled as a function of time while determining the two end points, then some otherwise valid data points would be interpreted as misfits.

The parameters can be solved using well-known NLLS solvers. For example, a separable non-linear least squares approach can be used where a bi-linear problem is solved to get x, y first, followed by $c_k$.

The second step of the IFM contamination estimation model includes fitting the $c_k$ obtained from the first step using a contamination model. For example, the error function is also a solution for well defined cases of WBM invasion, having a strong resemblance to the form of the sample quality function previously discussed for the case of OBM. FIG. 3 shows the results of a large number of sample quality simulations with WBM systems using the sample quality function discussed above based on the Error Function contamination function in Eq. (17). Typical ranges for $a_1$ and $a_2$ for WBM systems are:

$$0.50 \leq a_1 \leq 100, \text{ and}$$

$$0.25 \leq a_2 \leq 0.50.$$

Another possible contamination model is a logarithmic arctan function:

$$c(t) = \frac{1}{2} - \frac{1}{\pi}\arctan\left[a_2 \log\left(\frac{t}{a_1}\right)\right], \quad (28)$$

The IFM method described above can be modified without departing from the teachings of this disclosure as will be appreciated by those of skill in the art. For example, in alternate embodiments, the input data can be weighted based on flow rate, hydrogen index, fit error, noise level, and others. Also, contamination can be estimated in different embodiments either in the time-domain, or $T_1$ domain, where preferably the user can specify either the time or $T_1$ range. Additionally, while Eq. (27) solves for two endpoints, the IFM model could be extended in straightforward manner to the case of three or more fluids by weighting. Thus, a possible scenario is fluid 1 being clean crude from a previous logging station, fluid 2 being the OBM filtrate that enters when flow starts, and fluid 3 being crude at the current depth, which may have a different viscosity from fluid 1.

Summary of Contamination Estimation Using NMR Measurements

The following algorithm summary is provided for the convenience of the reader in the illustrative embodiment using viscosity as the fluid property being monitored, and indirect NMR measurements to determine these properties. The input curve for the algorithm is $T_{1Lm}$. In particular, from acquired echoes in an NMR measurement, the $T_1$ distribution is computed by standard inversion algorithms, and then converted to $T_{1Lm}$ using Eq. (5). Next, it is assumed that the sample being analyzed is a mixture of two fluids—the contaminant and the formation fluid. Using the $T_{1Lm}$ curve one can obtain viscosity indices for these fluids, i.e., the values of $\eta_1$—the viscosity of the contaminant, and $\eta_2$ as the viscosity of the native fluid. Subsequently, the volumetric fraction of the contaminant and the formation fluid at each experiment is computed by applying a fluid mixing-model. The algorithm can be summarized in the following steps:

(1) Read $T_{1Lm}$ data;
(2) Compute the viscosity index of the fluid mixture $\eta_m$ for each experiment by applying the oil viscosity formula in Eq. (6);
(3) In a least squares fashion, fit $\eta_m$ to a parameterized viscosity index function c(t) of a given structure (Eq. 12-16).
(4) Compute the viscosity indices of the contaminant: $\eta_1 = c(t)$, t=0; and of the formation fluid $\eta_2 = c(t)$, t=∞.
(5) Compute the contamination index for each experiment by applying a fluid mixing model in Eq. (8-11).

In the above summary, the time-function and mixing-model are uncoupled. It will be appreciated that both uncoupled and coupled estimates can be provided based on principles discussed above. In a particular embodiment, several tests may be performed to determine the estimation model that optimally fits the data.

It will be appreciated that in the embodiments discussed above the end point properties—either apparent viscosity or $T_1$ spectrum—are treated as unknowns. While this is generally true, there are some instances when there is a-priori information about the properties of one or more fluids. For example, if the application involves gas (methane) and OBMF, then the $T_1$ (or the $T_{1Lm}$, since it is uniexponential) of gas is known, and can be treated as a known-quantity, simplifying the inversion. In some cases, a-priori information can exist about the contaminant OBMF, its viscosity or $T_1$ spectrum may be treated as known. In either case, the a-priori information improves the performance of the inversion, since the number of unknowns is reduced.

Application of the Contamination Estimation Models

In another aspect, this disclosure also provides methods for applying the contamination estimation models to the non-ideal conditions encountered while drilling. The equation of the contamination estimation models are developed based on an assumption of ideal behavior of the formation fluids. One assumption of the contamination estimation models is that there are two end point fluids, e.g., the contaminant and the hydrocarbon. However, the fluid that is measured at the beginning of each experiment may not contain either of the end-point materials. The fluid measured in the experiments at earlier times may be the fluid left in the flow line from a previous station, possibly measured at a different depth where the reservoir fluid could be completely different. For the very first measurement using a new analyzer in the well, the fluid in the flowline may be water left in the tool during calibration in the shop. Also, contamination is usually modeled as a monotonic phenomenon, in that contamination is taken to decrease as a function of time as the pump-out time increases. For example, $T_{1Lm}$ (or its reciprocal) may actually decrease until the fluid left in the flowline is pumped out, then reverse direction during the relevant portion of the clean-up process.

An example of such behavior can be seen in the top graph of FIG. 4, where the diamonds and circles represent actual data points. The top graph shows a log-log plot of contamination estimation models in the specific embodiments to a viscosity vs. time measurement, where the diamonds (◊) and the circles (○) are data points, while the curve is the fit of a model to the data points. The middle graph shows spin-echo data from a number of experiments. These and other complications may result in the actual contamination trend not being monotonic. If left uncorrected, the artifacts due to flow rate changes may produce data points that are outside the expected range, yielding unreliable contamination estimates.

Accordingly, in a preferred embodiment, an inflection-point detection algorithm may be applied to identify the relevant time window that contains data from the fluids of interest. Once the relevant time window is identified, data outside this window can be excluded from the inversion. The application of an inflection-point detection algorithm to a data set is demonstrated in the top graph of FIG. 4, where the data points represented by diamonds are within the desired range, while the data points represented by circles are determined to be outside this range. Data points in the window that fall within the desired range are weighted more in application of the contamination estimation models as compared to the data points outside the window. In the embodiment illustrated in the top graph of FIG. 4, an arctan-like function is used in the weighting. The reliable and automatic identification of the relevant time window is significant to real-time measurements, since no expertise is required on the part of the user to define the preferred data range on which to perform the analysis.

Earlier contamination estimation models have been developed based on the assumption that the contamination approaches zero if pumping continues indefinitely (i.e., $c(\infty) \to 0$). See, e.g., U.S. Pat. Nos. 6,178,815; 6,274,865; 6,343,507 and 6,350,986, which are incorporated herein by reference. Unless the well is drilled under-balanced, this would generally not be the case. The overbalance pressure that exists in most wells allows a small amount of mud filtrate to continually leak through the mudcake. With sampling, the filtrate leakage near the probe would be diverted and mixed with the formation fluids entering the tool, causing some residual contamination. Factors that can influence this residual contamination include overbalance, permeability, and (to a lesser degree) anisotropy. The permeability influences how quickly the mudcake forms and the flow rate at which the formation tester can pump a sample. As a result, the residual contamination increases with reduced permeability. The residual contamination can be estimated, and in most cases is less than 1%.

The present disclosure also provides methods of adjusting the contamination models to take into account the residual contamination. Using additional simulations, it is possible to develop a correlation function, where the residual contamination (related to the overbalance and permeability) is estimated before pumping starts. The limits of the contamination estimation functions (e.g., Eqs. 12-18) used to estimate the contamination while pumping, i.e., the two end points, are then rescaled, so that the projected sample contamination is asymptotic to the residual contamination.

Comments and Algorithm Extensions

Fluid Properties

While the contamination estimation models described in the illustrative embodiment using viscosity and NMR measurements for illustration, the principles of this disclosure can be applied to any other physical parameters or measurements of the formation fluid that are sensitive to contamination. For example, resistivity, capacitance, density, viscosity, HI (hydrogen index), compressibility, speed of sound, and even the pumping pressures can be sensitive to changes in contamination. The specifics of the mixing rule(s) or contamination function models applicable in each case are believed within the scope of knowledge of a person of ordinary skill in the art and will not be considered in further detail. The interested reader is directed to the discussions in the references cited in Section "Viscosity Mixing Rules" and "Modeling the Contamination Function" above for background information.

The use of different fluid properties in accordance with the principles of this disclosure is illustrated using the Implicit LogMean $T_1$ approach, discussed above. Suppose that in a particular implementation, the choice of the contamination function model is the ArcTan model in Eq. (8). An error measure could be defined as:

$$\epsilon_k = c_k - d_k,$$

where $$c_k = x_3 + x_1 \arctan(t_k^{x_3}/x_2)$$

$$d_k = T_{1Lm,k}.$$

The elements of the vector of unknowns $x = (x_1, x_2, x_3, x_4)^T$ correspond to the parameters $(a_1, a_2, a_3, p)$ in the ArcTan Model. The objective function in a simplest form can be defined as:

$$\Phi(x) = \sum_{k=1}^{K} \epsilon_k^2$$

The task is then to find the vector x that minimizes the above function, like in any other least squares problem. While the illustrative embodiments using viscosity $d_k$ is the log mean of $T_1$, other parameters, such as log-mean $T_2$, log-mean D0, as well as the hydrogen index, pressure values, or others can be used instead. It will thus be appreciated that the approach proposed herein is not limited to a particular fluid property, or a particular modeling function but rather can be extended without due experimentation to different properties, different mathematical model functions or function combinations.

In accordance with another aspect of the disclosure it will be appreciated that in certain fluid mixtures one of these properties may be more sensitive than others to the contaminant. Accordingly, an array of instruments can be used in a preferred embodiment to measure individual properties and the approaches disclosed below applied to each measurement. In a specific embodiment, different contamination estimates can be combined into a single average contamination estimate. Individual contamination estimates may be weighted, preferably using nonlinear regression techniques. As is the case with MRILab® estimates of viscosity, the formation fluid properties can be more accurately predicted because the end points are used to determine the in-situ sample properties.

Multi-fluid Modeling

In another aspect, it will be appreciated that the mixing rules described in the above illustrative embodiments are applicable to two fluids—generally a contaminant and the native formation fluid. In certain applications, it may be advantageous to consider three different fluid types, for example, in the production of a well, where fluids of different viscosities are produced from different zones. It will be appreciated that in such cases, for example, a gas zone, and two oil zones may be encountered, where the oils have different viscosities. The viscosity mixing rules given for 2 fluids (Eqs. 8 thru 11), have counterparts for 3 or more fluids. For example, the 2-fluid mixing rule, referred to as Todd et al, given by $$\eta_m = \frac{\eta_1 \eta_2}{[s_1 \eta_2^{1/n} + s_2 \eta_1^{1/n}]^n},$$

where $s_1 + s_2 = 1$, can be extended for 3-fluids in the following way (Todd et al):

$$\eta_m = \frac{\eta_1 \eta_2 \eta_3}{[s_1 \eta_2^{1/n} \eta_3^{1/n} + s_2 \eta_1^{1/n} \eta_3^{1/n} + s_3 \eta_1^{1/n} \eta_2^{1/n}]^n},$$

where $s_1 + s_2 + s_3 = 1$.

It can be seen from the above that extension of the other mixing rules, for 3 or more fluids, in many cases is straightforward.

NMR Measurements of Viscosity

The relationship between viscosity and $T_{1Lm}$, as given in Eq. (6), strictly speaking applies for dead oils, generally not having any substantial portion of gas. The relationship is dependent on the Gas-Oil-Ratio (GOR), as shown in Eq. (7), if the oil is live. Since f(GOR) is not known at the time of the NMR measurement, the two end-point viscosities that are outputs of the contamination algorithm may not be correct in certain instances. For this reason, diffusion measurements, as discussed in Appendix A, may be used for viscosity determination, because the relationship between D0 and viscosity is fundamental and is governed by Eq. (1), whereas the relationship between $T_{1Lm}$ and viscosity is empirical.

It should be noted, however, that in not knowing f(GOR) does not adversely impact on the contamination estimates obtained in accordance with this disclosure, because whether the oil is "live" or "dead," the values for $T_{1Lm}$ of the fluid are inversely proportional to its viscosity, only the proportionality constant is different. Therefore, in the case where f(GOR) is unknown, while the end-point viscosities may be inaccurate, the saturations of the fluids (or the contamination levels) are still correct. Strictly speaking, therefore, the above disclosure is applicable to measurements of an apparent viscosity or a "viscosity index," instead of viscosity. It will be appreciated that in many instances the apparent viscosity from the contamination analysis will be correct, as in the case of higher viscosities (i.e., low GOR), where the $T_1$-viscosity relationship approaches that of the dead-oil relationship.

Effects of Flow on $T_1$ Data

FIG. 1A illustrates that the flow, dependent on the pumpout rate affects the $T_1$ distributions. The magnitude of the flow effect can be appreciated by comparing the $T_{1Lm}$ values, which are in the order of 3 seconds while flowing at 30 cc/min, to stationary values in the order of almost 10 seconds (near the bottom of the log). Faster flow rates result in less polarization in the case of long $T_1$s.

If the fluid is viscous, in which case the $T_1$ values are relatively short, the flow rate does not affect the $T_1$ distributions substantially, and the flow effect can be ignored. In a similar way, if the fluid has low viscosity (long $T_1$s), but the flow rate is low, then once again, the $T_1$ distributions are not affected for practical purposes. In either case, the effects of flow are minimal and no corrections are needed.

In accordance with another aspect, the contamination algorithms presented herein may function well without flow corrections to the data even in the worst case of long $T_1$s and high flow rates, as long as the transition from stationary to non-zero flow is made quickly and the flow rate is not varied for the remainder of the time. In such measurements, the most significant effect of flow is to change the apparent viscosity. The artifacts caused by high flow rates are analogous to that of viscosity in the case of dead vs. live oil. In similar fashion, while the apparent viscosity may not be close to the true viscosity, the volume fractions of the two end points, i.e., contamination is still accurate. It will be appreciated, however, that if the flow effects reduce the dynamic range in $T_{1Lm}$, the sensitivity of the contamination estimates may be reduced. These issues can be taken into account with proper adjustment of the pumpout rate of the device in operation.

EXAMPLES

Example 6.1

Figure 13:
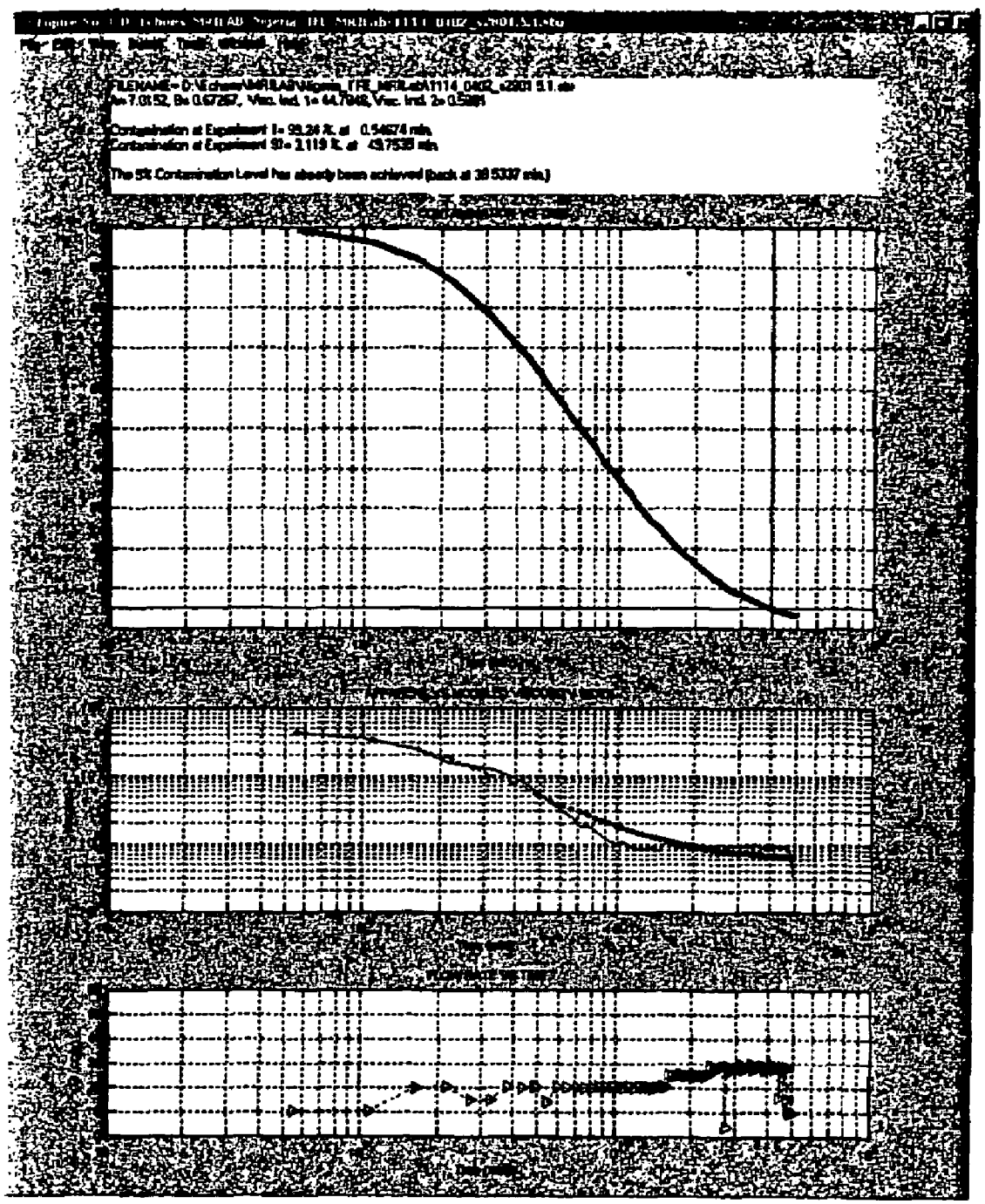
FIG. 13 shows the results of contamination estimation for the data shown in FIG. 1A using a Coupled Log-mean $T_1$ model.

The results of the contamination estimation for data shown in FIG. 1A using a CLMT1 contamination estimation model (Eq. (26)) are shown in FIG. 13.

In the top report section, several parameters and answers are listed. The results of the inversion, for the end-point viscosity indices, as well as the parameters $a_1$ and $a_2$ are listed. The contamination level at the first and the last experiments, in percent are also listed in the report section. Finally, the time estimate for reaching the contamination threshold is given at the bottom. In the example used, the 5% threshold was already achieved.

The second section contains a plot of the estimated contamination vs. time. The estimated contamination is about 2 percent towards the end of the measurement.

The third section is a plot of the input data (solid curve) vs. the fit (connected diamonds). The flow rate is shown in the bottom plot, for reference. In the third section, one can see the $T_1$ distributions for the two end members.

Example 6.2

The top graph of FIG. 4 shows viscosity vs. time data points (diamonds and circles) from an MRILab® Fluid analyzer, obtained from a well drilled with OBM. An inflection-point detection algorithm was applied to identify the relevant time window (diamonds) that contains data from the two fluids of interest. The data in the relevant window (diamonds) is weighted by an arc-tan function as compared to the data outside the window (circles).

The top graph of FIG. 4 also shows the results of the application of the $ELMT_1$ model to the data from the MRILab® (shown by the curve fit). The estimated contamination value of 4.7% is obtained from application of the $ELMT_1$ model, using a combination of the Modified Ahrrenius mixing rule in Eq. (11) and the ArcTan-Shifted 2 contamination model in Eq. (15). Independent laboratory results were obtained from the analysis of the actual fluid samples secured with the RDT. The laboratory measured contamination value is 4.0%.

Example 6.3

While the IFM is not suitable for OBM, it nevertheless gives results comparable to the MFM. The contamination estimation results using the IFM for the data shown in FIG. 1A can be seen in FIG. 14, where contamination is modeled using the error function (even though OBM is used during logging).

Figure 14:
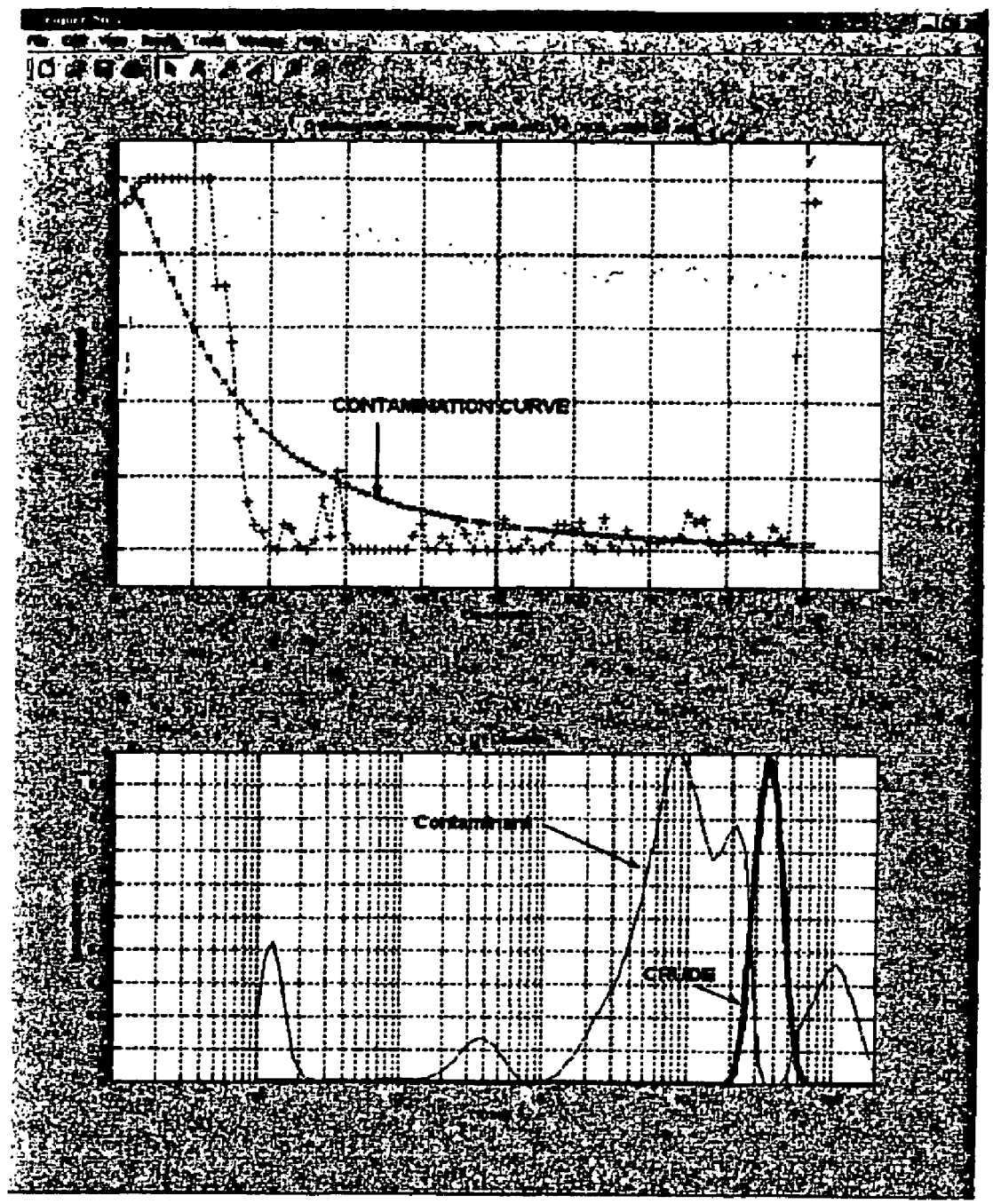
FIG. 14 shows the results of contamination estimation for the data shown in FIG. 1A using an immiscible fluid model.

The lower plot of FIG. 14 shows the $T_1$ distribution for the two end-members. It is interesting to note that the algorithm used in the analysis chooses the most commonly occurring $T_1$ spectrum for the crude (see FIG. 1A, experiment range 30 to 80), and has considered most everything else as a contaminant, including the very long $T_1$ values encountered only at the end of the measurement.

The upper plot shows the contamination values as a function of experiment number. The monotonically decaying smooth curve is the contamination curve. Towards the end of the measurement, contamination values are on the order of 2 percent. The results shown here are obtained by constraining the contamination values between 0 and 1, which explains the abundance of points occurring at 0 and 1.

The applicability of an IFM model to an OBM system is probably due to the nature of the fluids and the type of the data collected. Basically, when the two end points are very different, and one has waited long enough for clean up as in this example, any monotonically decaying function will show that contamination is low.

Appendix A

The following description summarizes equipment and methods used in the illustrative embodiment of the application, which relies on NMR measurements. The interested reader is directed for additional detail on NMR to the disclosure of the patents and publications set forth in the background section of the invention.

NMR Fluid Analyzer

Figure 5A:
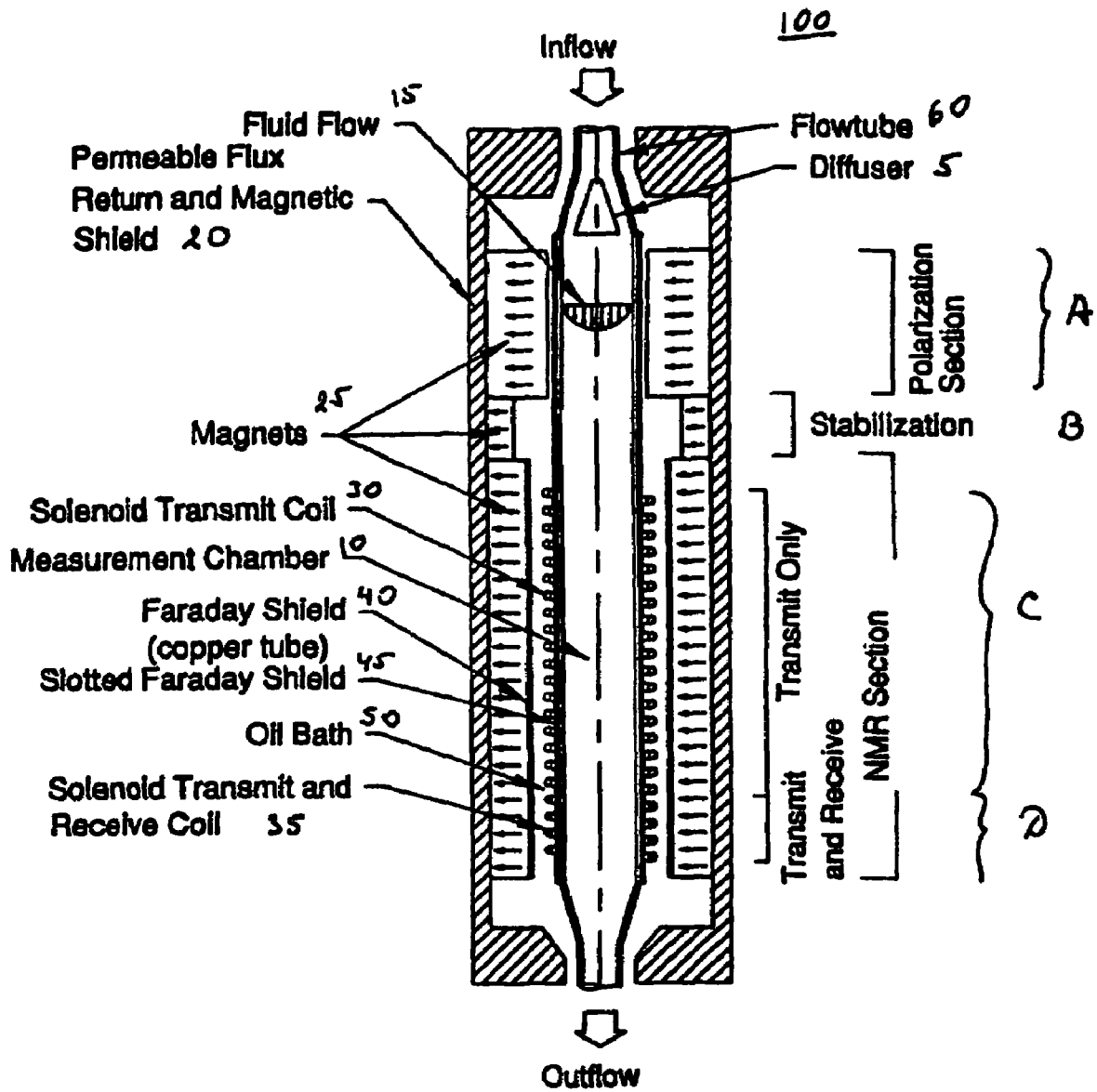
FIG. 5A is a schematic diagram of a downhole NMR fluid analyzer.
Figure 5B:
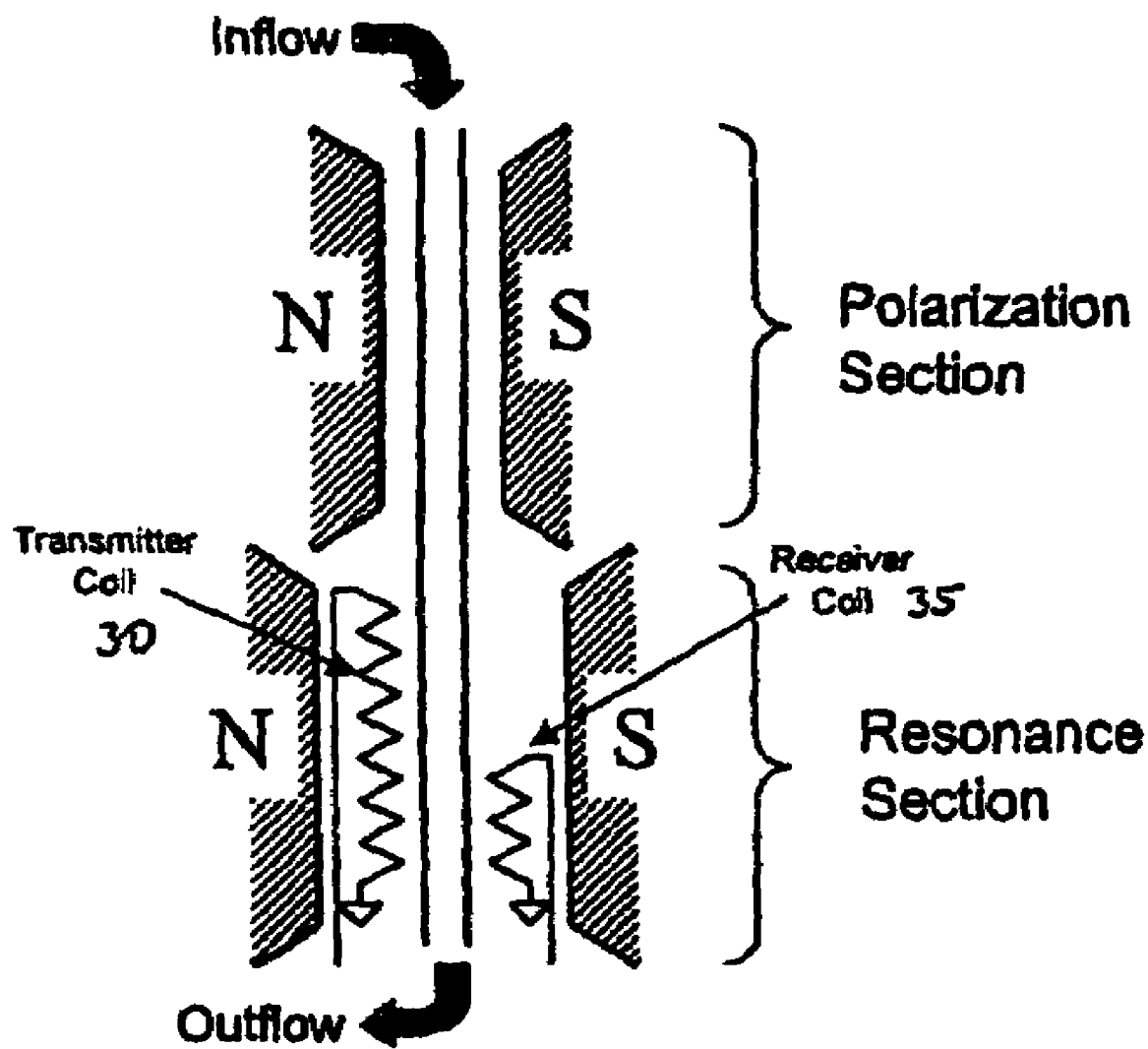
FIG. 5B is a simplified version.

FIGS. 5A and 5B show simplified diagrams of a downhole NMR fluid analysis apparatus, such as the MRILab®, that provides NMR measurements to which the contamination estimation methods of the present disclosure can be applied in an illustrative embodiment. Fluids enter the device at the top and pass through two sections, referred to as polarization and resonance sections, respectively. Measurements are performed as the fluid flow passes through the device. The fluid entering the system is initially subjected to a strong magnetic field to achieve rapid polarization of the hydrogen nuclei. NMR measurements take place in the lower section, where the field strength is lower. In a preferred embodiment, two separate radio frequency coils are used for pulse transmission and for reception. This split scheme allows for a transmitter coil 30 that is longer than the receiver 35. The practical effect of this split is that relaxation times estimates are less sensitive to the actual flow rate(s) because signals are received from only a portion of a larger volume of fluid that is being pulsed.

For a saturation-recovery $T_1$ experiment, a single pulse can be used to prepare a large volume, while the actual readout may happen over a smaller volume. This feature is used to render the measurement of $T_1$ relaxation times largely independent of flow velocities, up to a certain practical limit. Transmission and reception both operate at 4.258 MHZ at room temperature, consistent with 1,000 Gauss field strength. At higher temperatures, the operating frequency is reduced to track the reversible reduction in magnetic field strength.

The magnetic field in the measurement volume of the device shown in FIGS. 5A and 5B in general is not entirely uniform. This volume can be split conceptually into an interior region, where the field gradient is negligible, and a fringe region, where the field changes with an approximately uniform gradient. The fringe region may comprise about one third of the total sensitive volume. During $T_1$ measurements and at short pulse-to-pulse spacing (such as 0.25 ms), the effect of the gradient is not noticeable. To perform a diffusion measurement, the main flow is diverted and a sample is stagnated within the NMR chamber. Furthermore, the pulse-to-pulse spacing (Te) is increased to induce diffusion-dependent signal dephasing. The uniform and the fringe regions are large compared to the largest possible diffusion length; therefore, these regions are essentially isolated from each other for the duration of a single pulse-echo train.

Figure 6A:
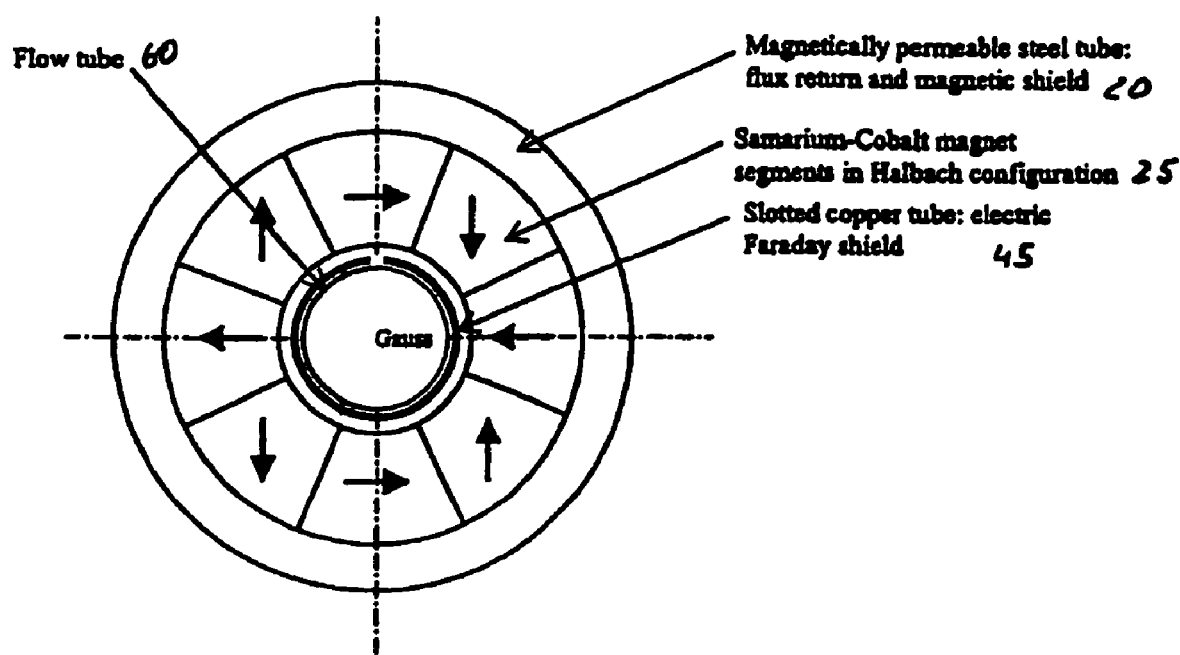
FIGS. 6A-6D illustrate horizontal cross sections of the analyzer shown in FIGS. 5A and B.

FIG. 6A is a detailed cross-sectional view of the polarization section of the apparatus that the flowing fluid encounters after it enters the measurement chamber. The purpose of this pre-polarization section is to polarize hydrogen nuclei in the fluid(s) as rapidly as possible, so that they will exhibit full polarization under the operating field. The flow tube 60, is made from ceramic, glass or PEEK material, and is surrounded by a Faraday shield 45. The magnet consists of segments 25 that are magnetized as indicated by the arrows and are made of material with very low temperature coefficient.

Figure 6B:
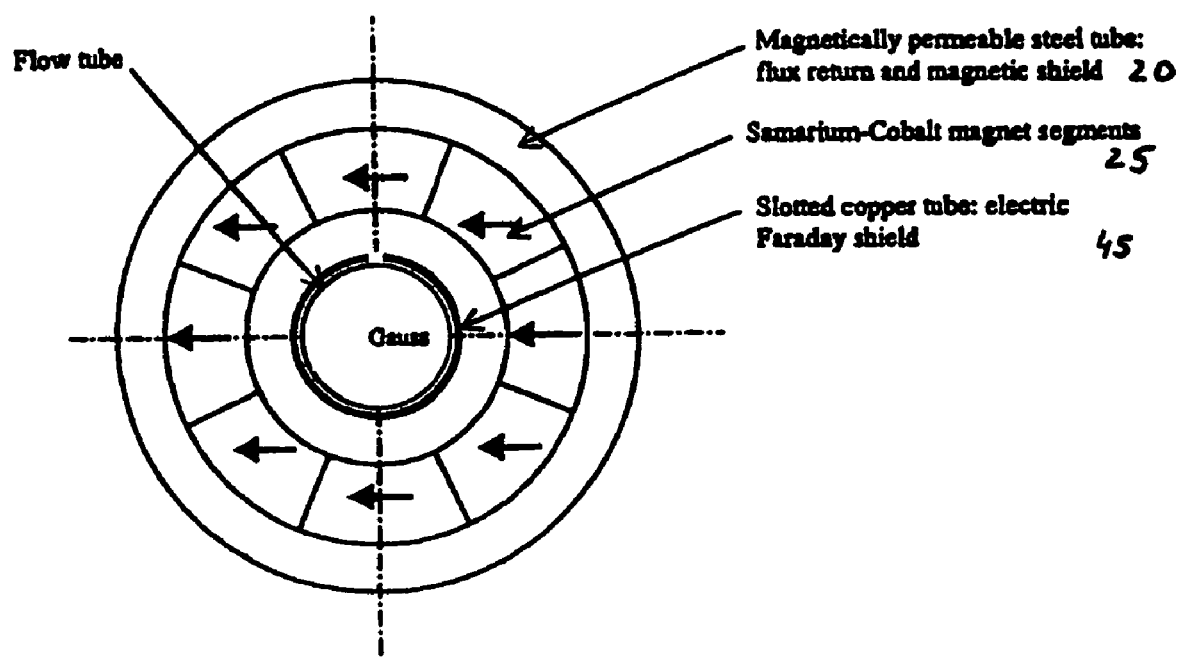

FIG. 6B is a detailed cross-sectional view of the second section of the apparatus, which is located between the polarization section and the measurement section(s) (labeled "Resonance Section" in FIG. 5B). The purpose of this section is to allow the hydrogen spins to settle to an equilibrium polarization that is close to a non-flowing magnetization corresponding to an external field of 1,000 Gauss.

Figure 6C:
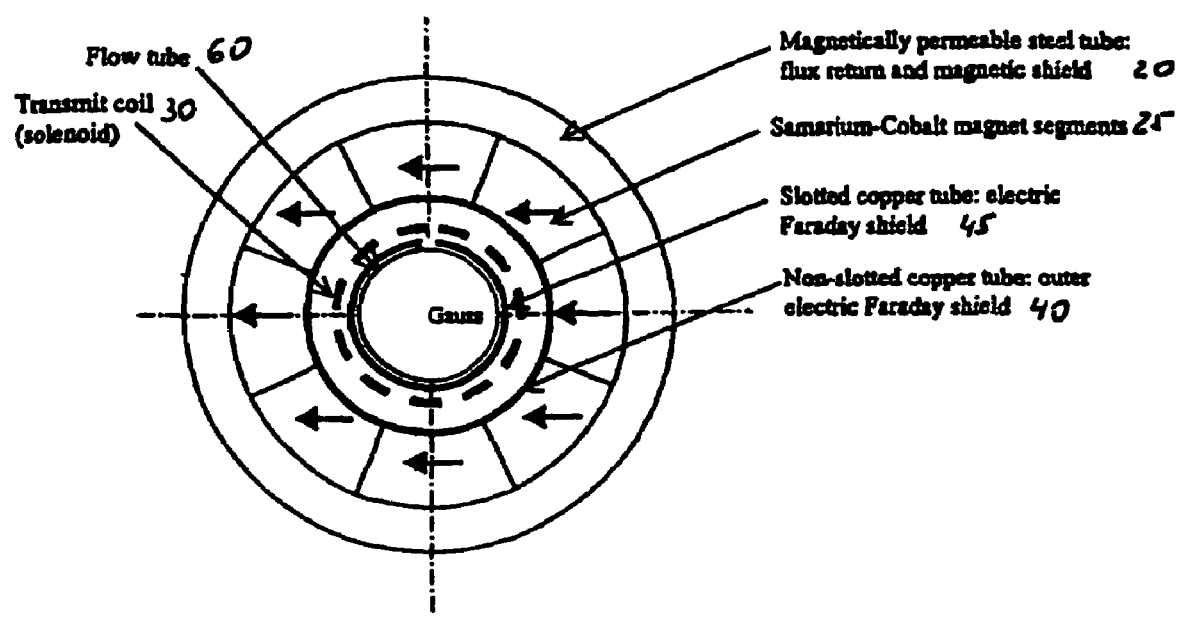
Figure 6D:
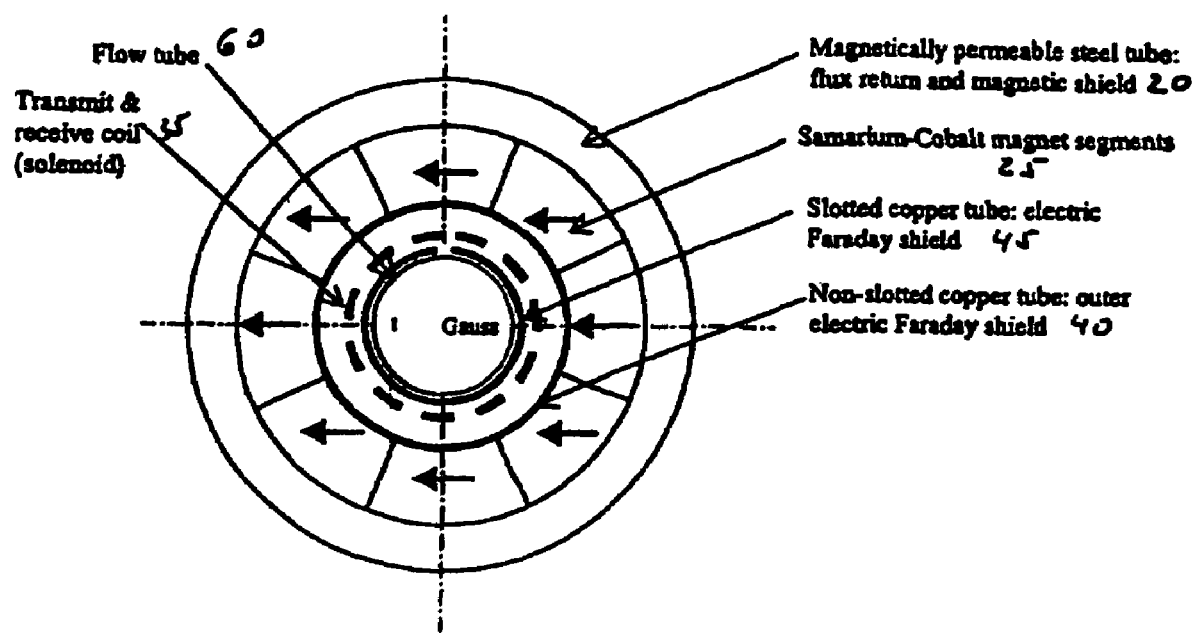

FIG. 6C is a detailed cross-sectional view of the transmit portion of the measurement section of the apparatus, which follows the stabilization section. FIG. 6D is a detailed cross-sectional view of the last section of the apparatus, which is the transmit/receive section. The NMR time constants $T_1$ of the fluid(s) under investigation are determined by varying the delay time between a broadband saturation pulse and a read-out sequence. If the flow velocity does not exceed 10 cm/s, the measurement is generally independent of the flow speed and of the flow profile.

Figure 7:
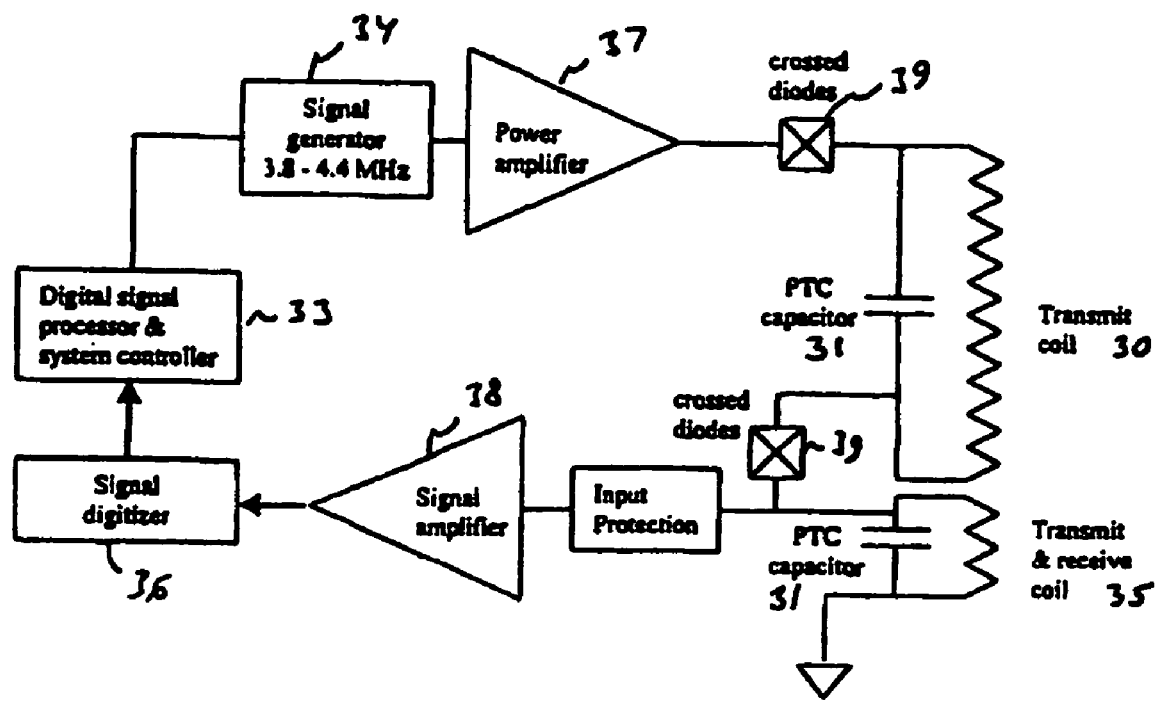
FIG. 7 illustrates a schematic block diagram of the electronics of the analyzer in one embodiment.

The electronics used in the NMR fluid analyzer, which is illustrated in a block diagram in FIG. 7, is similar to that of an NMR spectrometer. The comparatively low frequency of 4.2 MHz used in for some of the measurements allows many traditionally analog functions to be realized readily as digital signal processing (DSP) algorithms. A frequency source 34, controlled by a pulse programmer, sends its signal to a power amplifier 37, which in turn drives the transmitter antenna 30. All timing functions, like pulse widths and acquisition windows, are fully programmable. On the receive side, the signal from the receiver antenna 35 is amplified, synchronously demodulated and integrated. The system also performs its own calibration. All pertinent calibration factors are stored in the tool itself and after calibration echo amplitudes are reported on a scale of 0-2. The two coils of the device 30, 35 are connected to resonating capacitors 31. These capacitors are of the NPO (no temperature coefficient) and PTC type (positive temperature coefficient), shunted in parallel, as shown. The resultant temperature characteristic is such that with increasing temperature, when the static magnetic field weakens (typically 1% per 100° C.), the capacitance increases at twice the rate (typically 2% per 100° C.). The resultant LC circuit resonant frequency drops at half the capacitor rate (1% per 100° C.) and therefore follows the NMR resonance, making re-tuning of the circuit unnecessary.

In a transmit mode, the controller 33 gates the signal generator 34 of the apparatus and the power amplifier 37 to produce a radio frequency pulse in both coils. The high voltage applied causes all crossed diodes 39 to conduct, thereby connecting the two coils. In receive mode, the crossed diodes stop conducting and signal is only received from the lower coil 35. The signal is amplified, digitized and fed into the digital signal processor 33 for demodulation and further processing.

The MRILab® described above determines hydrogen density, self-diffusion rates and NMR relaxation rates of fluids during the pump-out phase, from which one can compute sample viscosity and GOR. By design, fluid samples are analyzed under true reservoir conditions and results are available substantially in real time. In particular, the MRILab® measures the hydrogen index and the NMR polarization time constant ($T_1$) of flowing fluids, which pass through the device. In the sensor section, the hydrogen in the fluid is first polarized by a set of magnets and then pulsed via an antenna coil to excite the magnetic resonance response. The excitation and refocusing pulses are fed to a long transmitter coil that traverses the magnet section. A smaller receiver coil, located at the bottom of the flow-tube, picks up the NMR echo. The separated coil arrangement permits NMR measurements while flowing. The timing sequences for the excitation pulses are field-programmable for additional flexibility. By default, the device records the NMR amplitude corresponding to a number of distinct wait times ranging from 1 millisecond to 16 seconds. The amplitudes are calibrated in hydrogen index units, where 1 unit equals the hydrogen density in water under atmospheric conditions.

The MRILab® can also be switched to $T_2$ mode of operation. The measurement of the signal decay time $T_2$ is flow-sensitive and is generally valid when a sample is stagnant within the MRILab®, at which time the NMR signal decay induced by self-diffusion can be observed. Diffusivity is inversely proportional to viscosity, a relationship that holds true in dead oils as well as in gas-oil mixtures.

Relaxation Time Measurements

Figure 8:
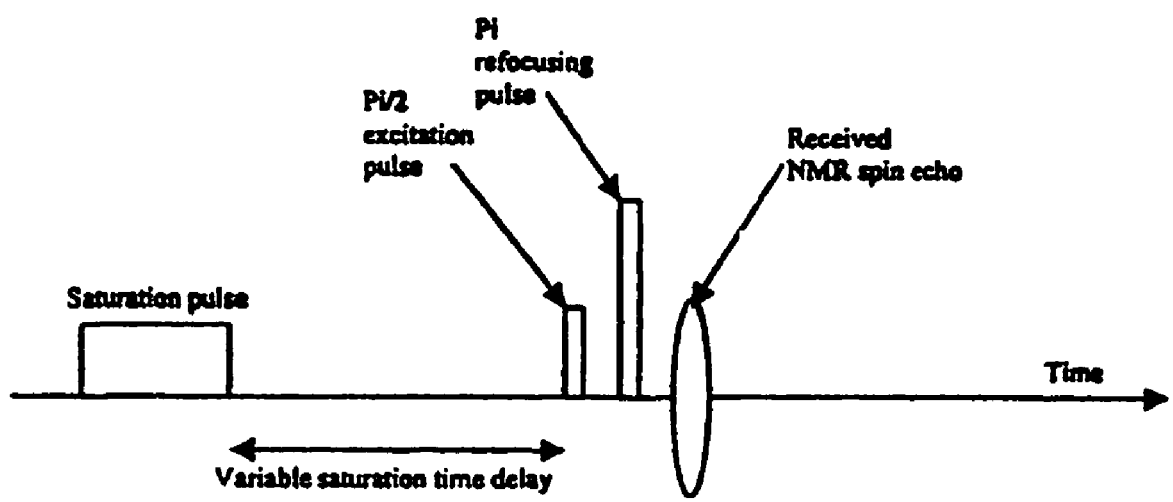
FIG. 8 illustrates a saturation recovery pulse sequence diagram used for $T_1$ measurements.

The $T_1$ relaxation times and hydrogen density can be measured continuously whether or not the fluid is stagnant or flowing. FIG. 8 illustrates a pulse sequence employed with the fluid analyzer in a specific embodiment. It will be appreciated that it is a standard saturation recovery sequence, where an initial saturation pulse is followed by a variable delay. In a preferred embodiment, the delay is programmable and is typically stepped through the values 1, 2, 4, 8, 16, 16384 ms in cyclical fashion. The recovered magnetization at the end of the delay is determined by a short read out sequence, consisting of two pulses and one spin echo. The height of the echo, if plotted as function of delay time, traces out a recovery curve that is converted into a $T_1$ distribution by standard inversion methods. In one embodiment, the inversion algorithm is a variant of the method employed to calculate $T_2$ distributions from wireline data, as disclosed in U.S. Pat. No. 5,517,115. With the above sequence it takes about 33 seconds to complete a measurement cycle. The signal-to-noise ratio of the system is so high that additional averaging may be unnecessary. The sequence described above is insensitive to fluid flow and can be used to continuously monitor the $T_1$ profile of pumped fluids. Other measurement sequences may be used in alternative embodiments.

More specifically, the $T_1$ measurement sequence is initiated by a frequency swept saturation pulse. The frequency is selected such that the entire range of frequencies in the resonance sections of the apparatus is affected. In a specific embodiment, this range is typically the NMR center frequency +/1% (4.2 MHz+/40 kHz). Pulse amplitude, frequency sweep rate and pulse length are adjusted to effect saturation.

As noted, following the saturation pulse, a variable delay is inserted. Preferably, consecutive measurements with delay values of 1 ms, 2 ms, 4 ms, . . . , up to 16384 ms are used. During these intervals, the nuclear magnetization builds up again to its equilibrium value. Also during this time, depending on the flow rate, fluid volume moves into the receiver coil volume, while unprepared fluid enters the resonance volume. As long as the flow rate is not high enough to allow unprepared fluid from the polarization section to enter the receiver coil section, it will be appreciated that the measurement is independent of the actual flow rate. After the saturation recovery delay, the instantaneous value of the nuclear magnetization is determined. This is done with a short pulse sequence, consisting of a $\pi/2$ pulse, followed by a $\pi$ pulse. The RF phase of these pulses is shifted by 90° against each other to cancel the effects of $B_0$ and RF field imperfections. This is equivalent to the start of a Carr-Purcell-Meiboom-Gill (CPMG) pulse sequence. The time between these pulses is typically 0.125 ms; a spin-echo forms 0.125 ms after the $\pi$ pulse. This echo is digitized, quantified and its amplitude is taken as a measure of the recovered magnetization as function of the saturation recovery delay. Note that the $\pi/2$ and $\pi$ pulses can be narrow band and need not be frequency swept. The reason is that they are only relevant for the receiver coil section which has a very tightly controlled field and resonance frequency distribution.

Figure 9:
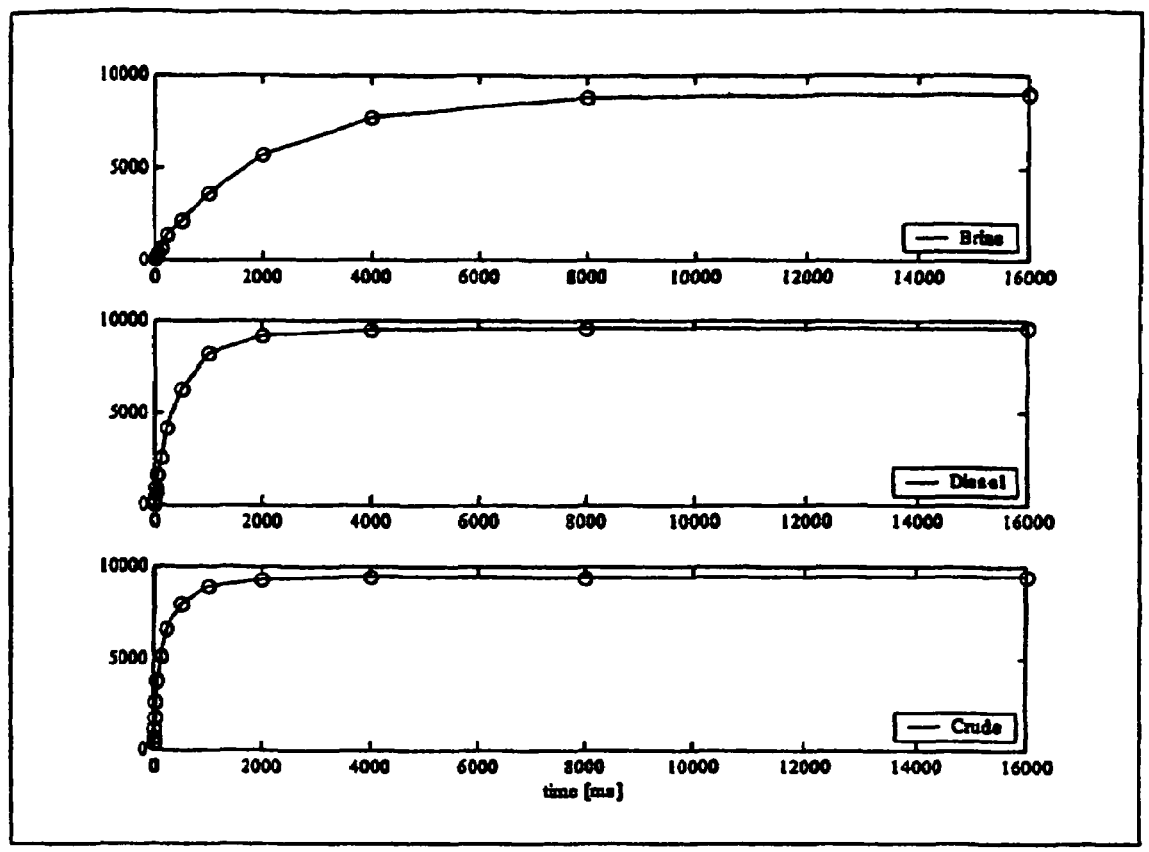
FIG. 9 shows $T_1$ saturation-recovery data for three different fluids as seen in an NMR fluid analyzer.
Figure 10:
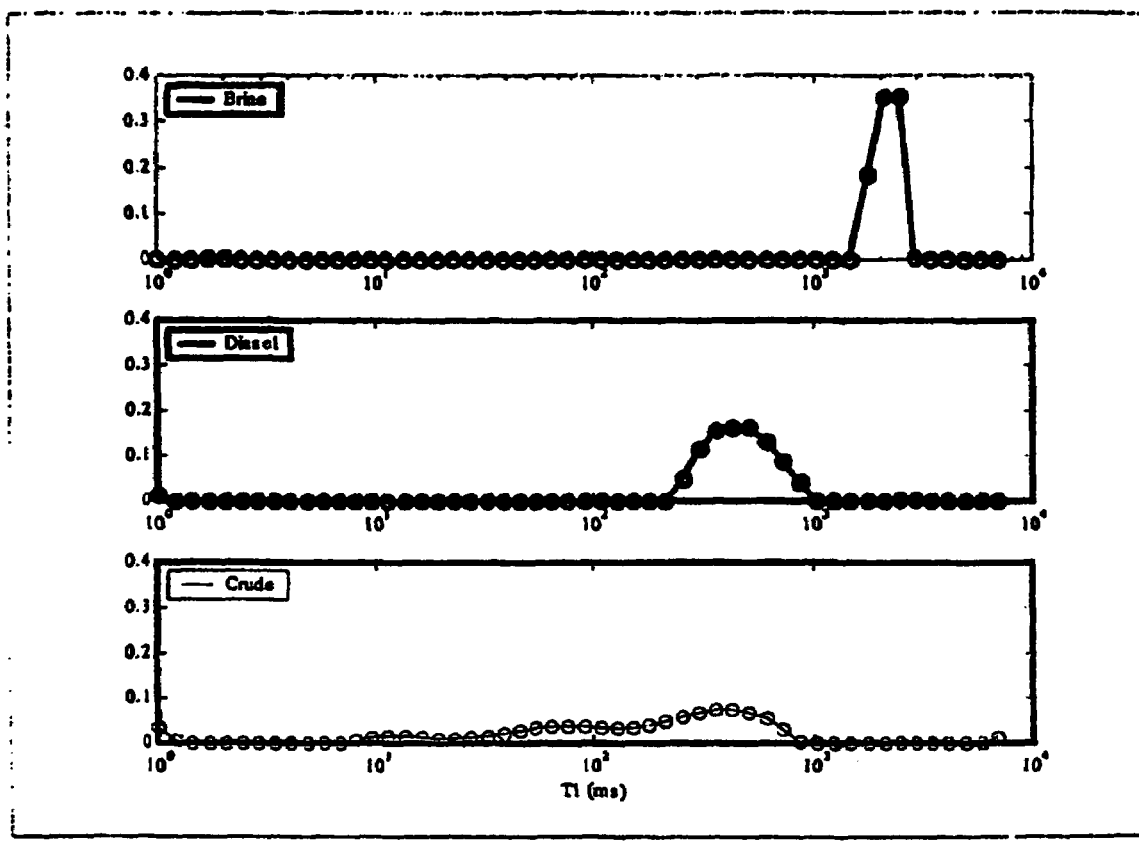
FIG. 10 shows a re-plot in the $T_1$ domain of the data shown in FIG. 9.
Figure 11:
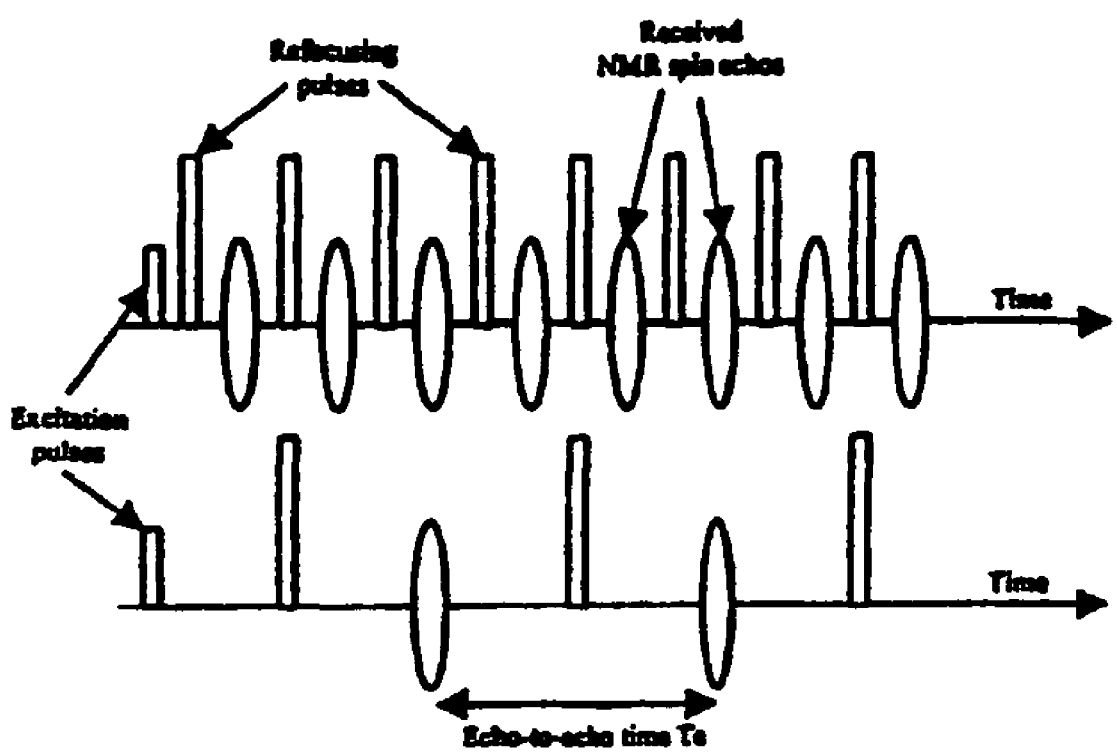
FIG. 11 illustrates a pulse sequence employed for diffusivity measurements.

Examples of $T_1$ distributions for some example fluids are shown in FIGS. 10 and 11. The data points were acquired according to the sequence in FIG. 8 and inverted from the time domain to the $T_1$ domain. The horizontal axis, "time,"

in FIG. 9 denotes the time elapsed between the saturation pulse and the readout sequence, the vertical axis is signal amplitude in arbitrary units. The results are easier to interpret after inversion from time domain to $T_1$ domain, as shown in FIG. 10. In this example 53 points are specified for the inversion result. The single, sharp peak at 2-3 seconds is characteristic of water, the rounded peak in the "oil window" 0.5-1 second indicates oil and the broad response from the crude oil in the bottom panel is characteristic for complex hydrocarbons. The figure shows examples of $T_1$ saturation recovery data for three different fluids: brine, Diesel oil and a crude oil.

The data points illustrated have been acquired by circulating different fluids through the analyzer. Shown from top to bottom are: water (mild brine) with a single relaxation peak in the "water window" at 2 seconds; next a simple hydrocarbon (diesel) with a single relaxation peak in the "oil window" at 0.5-1 second; and a complex hydrocarbon (crude), which shows a characteristic asymmetric distribution that starts in the few tens of milliseconds and extends to the "oil window." These samples were under atmospheric conditions at ambient temperature. At elevated temperatures, Eq. (2) predicts an increase in $T_1$ proportional to the absolute temperature in addition to increases due to reduction in viscosity.

The determination of long relaxation times no longer depends on how long an echo train persists. In the implementation discussed above, small perturbations in the applied field have relatively limited effect. Additionally, the saturation pulse prepares a much larger sample volume than what is actually used for the readout portion. Therefore, as long as the flow rate is low enough, and the readout is based on a fluid sample that was present anywhere within the resonance regions during the saturation pulse, the measurement is valid.

In contrast to $T_1$, the $T_2$ parameter generally cannot be determined on a flowing sample. Distributions of $T_2$ times are determined by standard CPMG sequences on samples that have been stagnated momentarily. Stagnation can be achieved by closing a valve below the analyzer apparatus and diverting the flow stream around the sample chamber. The time required for a $T_2$ measurement is almost entirely determined by the polarization time ("wait time") and is on the order of several seconds.

Hydrogen Density Measurements

The hydrogen density or the total number of hydrogen atoms within the measurement volume is a by-product of any $T_1$ or $T_2$ measurement. It can be represented as the area under any $T_1$ distribution and is typically normalized to the hydrogen density of reference oil at measurement temperatures. At room temperature, the reference oil and water have the same hydrogen density. The reported number is the relative hydrogen index (HI) in the range 0-2, with accuracy around 1%.

Hydrogen density can be automatically converted to hydrogen index (HI), which is the hydrogen density of a material relative to that of water at ambient conditions. The spin density of the fluid is proportional to the hydrogen index. Under the assumption that the oil contains only hydrogen and carbon atoms, the mass density $\rho_m$, the hydrogen index, and the hydrogen-to-carbon ratio R are related as follows:

$$HI \approx \rho_m 9R/(12+R) \quad (29)$$

See, for example, Zhang et al., (1998), "Some Exceptions to Default NMR Rock and Fluid Properties, Paper FF: SPWLA." presented at the 39$^{th}$ Annual Logging Symposium, Keystone, Colo., May 26-29. Since the hydrogen index is measured, either the mass density or the hydrogen-to-carbon ratio can be computed from an estimate of the other variable.

It has been reported that most saturated hydrocarbon liquids have relative hydrogen indices of 1 within +/−5%. The hydrogen density in gases is significantly lower due to the overall lower density. Thus, a depressed hydrogen index serves as a first-order alert to the presence of gas and a change in the relationship between $T_1$ and viscosity. Appel et al. reported a reduction of about 20% on live oil samples at 180° F. (See Appel et al., "Reservoir Fluid Study by Nuclear Magnetic Resonance," Paper HH: SPWLA, presented at the 41$^{st}$ Annual Logging Symposium, Dallas, Tex., Jun. 4-7, 2000)). Under the assumption that all gas is methane ($CH_4$), the observed hydrogen index can be approximated as follows:

$$HI = x(9/4\rho) + (1-x)1, \quad (30)$$

where x is the volumetric gas fraction ($m^3/m^3$) and $\rho$, in $g/cm^3$, is the density of methane. The density of methane follows from its temperature and pressure, and Eq. (30) can be used to derive a first-order approximation for the gas fraction x.

Diffusion Measurements

Diffusion measurements can be performed using the NMR fluid analyzer using steady-gradient spin-echo (SGSE) experiments. The experiments require that the fluid flow is temporarily stopped. The concept of using the fringes of a uniform field volume for diffusometry derives from so called SSF-SGSE methods. The main advantage of the SGSE method over pulsed-field gradient spin-echo (PFGSE) difflusometry is instrumental simplicity and superior stability. The main drawback is a limit on sensitivity, which, for the downhole implementation, is approximately $10^{-6}$ $cm^2/s$.

The sensitive volume of the apparatus can be divided into an interior, homogeneous region and an exterior gradient region. The field in the fringe volume, which makes up about ⅓ of the total volume, can be approximated by a single field gradient value $G_0$. At short echo spacing (0.25 ms), the effect of the field gradient is too small to be relevant. The pulse sequence used both for diffusion measurements and for diffusivity calibration is shown in FIG. 11.

In particular, two CPMG sequences with a short echo spacing (typically 0.25 ms) and a long spacing ($T_e$) are alternated. The long echo spacing is selected as an integer multiple of the short spacing. In this case, echoes line up in time, i.e., occur at the same elapsed time, since the excitation pulse and the ratio of their amplitudes can be formed.

For a formation fluid with a given relaxation time $T_2$ and diffusivity D, the two echo trains for the short and the long echo spacing can be described as follows:

$$A_1 = I_H \exp(-t/T_2)$$

$$A_2 = I_H K_0 \exp(-t/T_2)\exp(-t/T_D) + I_H(1-K_0)\exp(-t/T_2) \quad (31)$$

where $$1/T_D = 1/12(\gamma G_0 T_e)^2 D. \quad (31)$$

The relations also apply for an arbitrary distribution of times $T_2$.

The system parameter $K_0$ is the gradient volume divided by the total volume. The hydrogen gyromagnetic ratio $\gamma$ is equal to 26,754 rad/s/gauss. Both $K_0$ and $G_0$ are temperature-dependent and are determined during calibration. The diffusivity D is derived from Eq. (31) by taking the ratio of corresponding echoes, as follows:

$$A_2/A_1 = K_0 \exp(-t/T_D) + (1-K_0) \quad (32)$$

This curve is fit to a uni-exponential model plus an offset.

Figure 12:
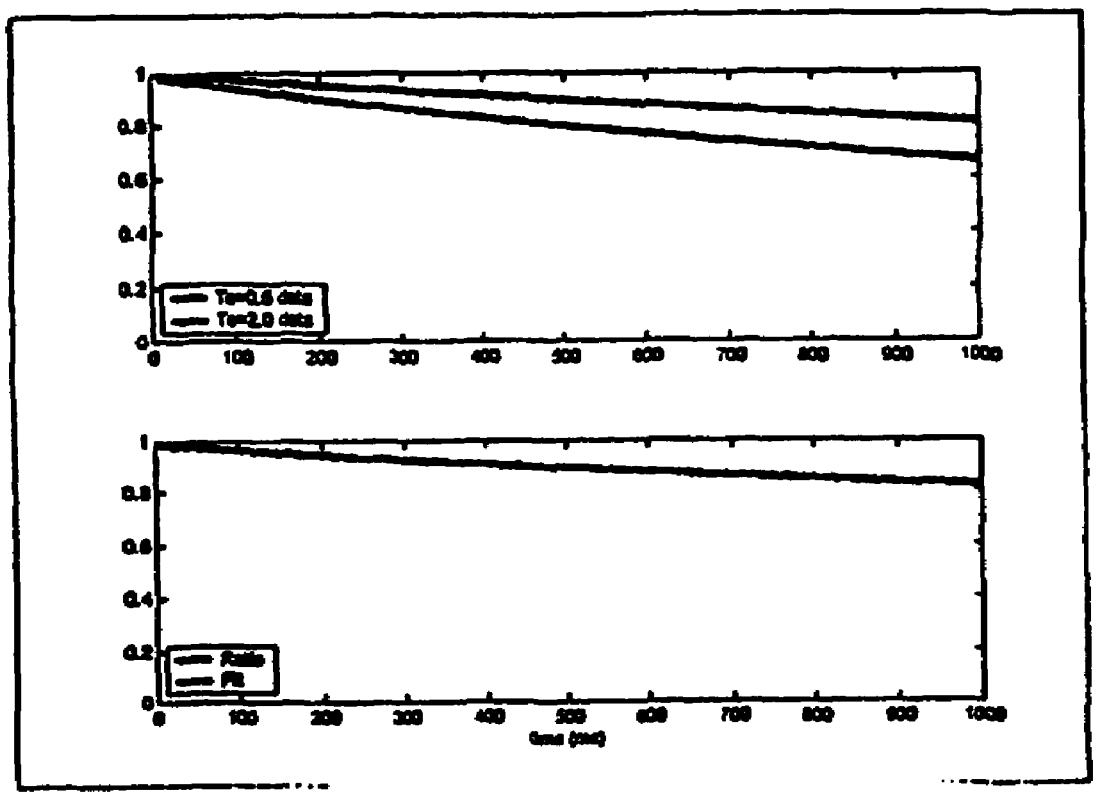
FIG. 12 shows a diffusivity measurement.

In the upper graph of FIG. 12, the two curves are the $A_1$ and $A_2$ signals for water at room temperature. The lower graph of FIG. 12 is the ratio curve and the best fit uni-exponential model. Since D for water is known as $2.5 \times 10^{-5}$ cm$^2$/s, these curves determine the calibration parameters $G_0$ and $K_0$.

The two curves in the upper graph of FIG. 12 are spin echo amplitudes at different echo spacings. The accelerated decay for the longer spacing is a manifestation of diffusion in the gradient region of the magnetic field. The ratio curve (lower graph) is the sum of an exponential and a constant term, corresponding to the gradient field region and the uniform field region, respectively. The best fit model curve is also plotted; however, it is indistinguishable from the data.

In a preferred embodiment, viscosity is determined as follows:

$$\eta = 5 \times 10^{-8} T/D \quad (33)$$

In this expression, the viscosity $\eta$ is measured in cp, the temperature T in Kelvin and the diffusivity D in cm$^2$/s. The temperature may be obtained from the RDT fluid temperature sensor. The proportionality factor is determined by fitting Eq. (1) to data from pure alkanes and methane alkane mixtures.

Although the present invention has been described in connection with the preferred embodiments, it is not intended to be limited to the specific form set forth herein, but on the contrary, it is intended to cover such modifications, alternatives, and equivalents as can be reasonably included within the spirit and scope of the invention as defined by the following claims.

What is claimed is:

1. A method for estimating levels of contamination in borehole fluids, comprising the steps of:
   (a) providing a first mathematical contamination function model which expresses a time behavior of one or more fluid properties of a mixture of formation fluids and contamination fluids drawn from a borehole, where said one or more fluid properties are sensitive to the fraction of contamination fluids in the mixture;
   (b) providing a second mathematical mixing law function model expressing at least one of said one or more fluid properties of a fluid mixture in terms of corresponding properties of formation fluids and contamination fluids in the mixture;
   (c) drawing fluids from the borehole into a fluid analyzer;
   (d) measuring at least one of said one or more properties of the drawn fluids by the analyzer; and
   (e) estimating the level of contamination in the fluids drawn from the borehole at one or more points in time based on the at least one measured fluid property and the provided mathematical models in step (a) and step (b).

2. The method of claim 1, wherein the provided mathematical models apply to miscible fluid contamination.

3. The method of claim 1, wherein the provided mathematical models apply to immiscible fluid contamination.

4. The method of claim 1, wherein the measured property of the drawn fluids is viscosity.

5. The method of claim 4, wherein viscosity is measured using nuclear magnetic resonance (NMR) measurement.

6. The method of claim 5, wherein the NMR measurement is one or both of: the spin-lattice relaxation time $T_1$ and spin-spin relaxation time $T_2$.

7. The method of claim 6 further comprising the step of computing log-mean values of the $T_1$ and/or $T_2$ relaxation times.

8. The method of claim 5, wherein the same mathematical model in step (a) is applied to two or more bands of a $T_1$ spectrum.

9. The method of claim 5, wherein two or more different mathematical models in step (a) are applied to at least one band of the $T_1$ spectrum.

10. The method of claim 7, wherein the log-mean values are computed using the expression:

$$\log(T_{1Lm}) = \frac{\sum_j a_j \log(T_{1j})}{\sum_j a_j},$$

where $a_j$ are the amplitudes of a given $T_1$ spectrum, and j is the number of $T_1$ bins used in the inversion.

11. The method of claim 4, wherein the first contamination function model provided in step (a) is one or more of: Arctan, Exponential, Arctan-shifted 1, Arctan-shifted 2, Arctan-shifted 3, and the Error Function models.

12. The method of claim 1, wherein the measured property of the drawn fluids is a physical property of the fluid.

13. The method of claim 12, wherein the measured property of the drawn fluids is one or more of: resistivity, capacitance, density, viscosity, hydrogen index, compressibility, speed of sound, pumping pressures, or optical density.

14. The method of claim 4, wherein a viscosity mixing law used in the second mathematical model is one of (i) Todd et al.; (ii) Power-Law, (iii) Arrhenius, or (iv) Modified Arrhenius.

15. A method for downhole formation testing, comprising the steps of:
   (a) providing measurement signals corresponding to a mixture of formation fluids and contamination fluids drawn from a borehole, the mixture entering a downhole fluid analyzer;
   (b) based on the provided measurement signals, determining parameters of a contamination function, which expresses the time behavior of one or more fluid properties of the fluid mixture drawn from the borehole;
   (c) computing from the determined contamination function of a value estimate of said one or more fluid properties for at least one low level of contamination and for at least one high level of contamination; and
   (d) computing a contamination index for the mixture of fluids drawn from the borehole at different time instants based on the computed value estimates and a fluid mixing law relating properties of the drawn fluids in terms of the corresponding properties of the formation fluids and the contamination fluids.

16. The method of claim 15, wherein the measurement signals are nuclear magnetic resonance (NMR) signals.

17. The method of claim 16, wherein the NMR measurement signals correspond to one or both of: the spin-lattice relaxation time T1 and spin-spin relaxation time T2 of the fluids drawn from the borehole.

18. The method of claim 17 further comprising the step of computing a log-mean value of at least one of the spin-lattice relaxation time T1 and spin-spin relaxation time T2 of the fluids drawn from the borehole, and using the computed log-mean value to determine parameters of the contamination function.

19. The method of claim 17, wherein a fluid property of the mixture in step (b) is viscosity.

20. The method of claim 18, wherein in step (c) a value estimate is obtained for a fluid property at a zero contamination level and at a 100% contamination level.

21. The method of claim 15, wherein the property of the drawn fluids in step (b) is one or more of: resistivity, capacitance, density, viscosity, hydrogen index, compressibility, speed of sound, pumping pressures or optical density.

22. The method of claim 21, wherein the fluid mixing law is empirically derived.

23. The method of claim 21, wherein the fluid mixing law is non-linear.

24. The method of claim 21, wherein the fluid mixing law is linear.

25. The method of claim 15, wherein the property of the drawn fluids in step (b) is viscosity, and a viscosity mixing law used in step (d) is one of: (i) Todd et al.; (ii) Power-Law, (iii) Arrhenius, or (iv) Modified Arrhenius.

26. The method of claim 15, wherein the fluid property in step (b) is viscosity and the contamination function is one or more of: Arctan, Exponential, Arctan-shifted 1, Arctan-shifted 2, Arctan-shifted 3, and the Error Function.

27. The method of claim 18, wherein the log-mean value is computed using one or more subbands in the corresponding T1 or T2 spectrum of the NMR signals.

28. The method of claim 27, wherein two or more subbands of the corresponding NMR spectrum are combined either linearly or nonlinearly.

29. An apparatus for estimating levels of contamination of formation fluids in a borehole, comprising:
  (a) means for providing a mathematical model comprising a contamination function which expresses the time behavior of one or more fluid properties of a mixture of formation fluids and contamination fluids drawn from the borehole, where said one or more fluid properties are sensitive to the fraction of contamination fluids in the mixture, and a mixing law describing at least one of said one or more fluid properties of the drawn fluids in terms of the corresponding properties of the formation fluids and the contamination fluids;
  (b) means for drawing fluids from the borehole into a fluid analyzer;
  (c) means for measuring at least one of said one or more properties of the drawn fluids by the analyzer; and
  (d) means for estimating the level of contamination in the fluids drawn from the borehole at one or more time intervals based on the at least one measured fluid property and the provided mathematical model.

30. A computer-usable medium having computer-readable program code thereon for use with fluid analyzers, the program code including code structured to:
  (a) collect measurement signals corresponding to a mixture of formation fluids and contamination fluids drawn from the borehole and entering a downhole fluid analyzer;
  (b) determine parameters of a contamination function, which expresses the time behavior of one or more fluid properties of a the mixture drawn from the borehole, based on the collected measurement signals; and
  (c) based on a fluid mixing law for the one or more fluid properties determined in (b) provide an estimate of at least one of (i) the level of contamination, or (ii) the pumping time for reaching a given level of contamination.

31. The computer-usable medium of claim 30, where at least one mathematical model comprises a viscosity mixing rule.

32. The computer-usable medium of claim 30, wherein in (c) the fluid mixing rule is a viscosity mixing rule and is one or more of: (i) Todd et al.; (ii) Power-Law, (iii) Arrhenius, or (iv) Modified Arrhenius.

33. The computer-usable medium of claim 30, wherein the measurement signals are NMR signals.

34. The computer-usable medium of claim 30, wherein the fluid property is viscosity, and the contamination function is one or more of: Arctan, Exponential, Arctan-shifted 1, Arctan-shifted 2, Arctan-shifted 3, and the Error Function models.

* * * * *